(12) United States Patent
Cleveland et al.

(10) Patent No.: US 9,186,163 B2
(45) Date of Patent: Nov. 17, 2015

(54) METHODS AND DEVICES FOR FORMING BONE TUNNELS

(75) Inventors: Benjamin Cleveland, North Grafton, MA (US); Kristian DiMatteo, Waltham, MA (US); Erik S. Sojka, Dighton, MA (US); Christopher G. Weinert, Mansfield, MA (US); Jose E. Lizardi, Walpole, MA (US)

(73) Assignee: DePuy Mitek, LLC, Raynham, MA (US)

( * ) Notice: Subject to any disclaimer, the term of this patent is extended or adjusted under 35 U.S.C. 154(b) by 538 days.

(21) Appl. No.: 13/487,586

(22) Filed: Jun. 4, 2012

(65) Prior Publication Data

US 2013/0325011 A1    Dec. 5, 2013

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/17* | (2006.01) | |
| *A61B 17/16* | (2006.01) | |
| *A61B 17/04* | (2006.01) | |
| *A61B 17/86* | (2006.01) | |
| *A61B 17/88* | (2006.01) | |

(Continued)

(52) U.S. Cl.
CPC ......... *A61B 17/1796* (2013.01); *A61B 17/0482* (2013.01); *A61B 17/1684* (2013.01); *A61B 17/1714* (2013.01); *A61B 17/0485* (2013.01); *A61B 17/86* (2013.01); *A61B 17/8875* (2013.01); *A61B 2017/00407* (2013.01); *A61B 2017/1778* (2013.01); *A61F 2002/0852* (2013.01); *A61F 2002/0888* (2013.01)

(58) Field of Classification Search
CPC ........... A61B 17/1697; A61B 17/1796; A61B 17/8861; A61B 17/0642; A61B 17/1714; A61B 17/04; A61B 17/0482; A61B 17/0483; A61F 2/0805; A61F 2002/0841
USPC .......................................................... 606/98
See application file for complete search history.

(56) References Cited

U.S. PATENT DOCUMENTS

| | | |
|---|---|---|
| 5,234,434 A | 8/1993 | Goble et al. |
| 5,403,322 A | 4/1995 | Herzenberg et al. |

(Continued)

FOREIGN PATENT DOCUMENTS

| | | |
|---|---|---|
| EP | 0 442 182 A1 | 8/1991 |
| WO | 2010/056787 A2 | 5/2010 |

OTHER PUBLICATIONS

U.S. Appl. No. 13/216,947 entitled, "Cross Pinning Guide Devices and Methods," filed Aug. 24, 2011.

*Primary Examiner* — Sameh Boles

(57) ABSTRACT

Methods and devices are provided for forming bone tunnels. In general, the methods and devices allow multiple converging tunnels to be formed in bone, such as in an arthroscopic surgical procedure, e.g., a rotator cuff repair surgical procedure. One or more sutures can be advanced through the converging tunnels, and the suture(s) can be coupled to tissue. The suture(s) with the tissue coupled thereto can be tensioned, thereby helping to maximize an amount of the tissue in contact with the bone. In an exemplary embodiment, a guide device is provided that can be configured to allow a first tunnel to be formed in bone and to allow a plurality of additional tunnels to be formed in the bone at predetermined angular positions relative to the first tunnel such that each of the additional tunnels can extend transverse to the first tunnel and intersect the first tunnel.

17 Claims, 31 Drawing Sheets

(51) Int. Cl.
    *A61B 17/00*    (2006.01)
    *A61F 2/08*    (2006.01)

(56)        References Cited

U.S. PATENT DOCUMENTS 6,066,173 A  *  5/2000  McKernan et al. ........ 623/13.14

7,192,432 B2     3/2007  Wetzler et al.
    7,842,042 B2    11/2010  Reay-Young et al.
    2003/0135211 A1  7/2003  Cho
    2007/0233151 A1 10/2007  Chudik
    2010/0121339 A1 * 5/2010 Whittaker et al. ............... 606/98
    2013/0110119 A1 * 5/2013 Atkinson et al. ................ 606/98

* cited by examiner

METHODS AND DEVICES FOR FORMING BONE TUNNELS

FIELD OF THE INVENTION

The present invention relates generally to methods and devices for forming bone tunnels, and in particular to forming intersecting bone tunnels.

BACKGROUND OF THE INVENTION

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A variety of injuries and conditions require repair of soft tissue damage, or reattachment of soft tissue to bone and/or surrounding tissue. One example of otherwise healthy tissue being torn away from a bone is a shoulder rotator cuff tendon being partially or completely torn from a humerus (a rotator cuff tear). Surgery is often required to reattach the tissue to the bone to allow healing and reattachment to occur. A number of devices and methods have been developed for performing these surgical repairs, such as screws, pins, staples, cement, suture anchors, and sutures.

One method of repairing damaged soft tissue is to form a receiving hole into the bone, e.g., with an awl, tap, or drill, and then a bone anchor is inserted into the hole using an installation tool that is effective to lock the bone anchor within the bone hole. The free ends of the suture can then be passed through or around tissue and tied to secure the tissue to the bone. Alternatively, in some soft tissue reattachment procedures, the soft tissue can be moved into position over the bone, and a hole may be formed through the tissue and then an aligned hole formed through the bone. A bone anchor can then be passed through the tissue and deployed into the bone. The free end of the suture is then tied to secure the tissue to the bone. In either procedure, the knotting process can be difficult and tedious, particularly during laparoscopic or arthroscopic procedures, where the surgeon must remotely manipulate the suture using tools inserted through an access tube. Such procedures often require the use of multiple bone anchors and multiple sutures requiring multiple knots to securely attach the tissue to bone and prevent the risk of tearing. Additionally, passing one or more sutures through the tissue can require extensive, time-consuming manipulation of the tissue and suture(s).

Another method of repairing damaged soft tissue is to form multiple holes into bone, with the holes converging. One or more sutures passed through or around tissue can be passed through the multiple holes and tied to secure the tissue to the bone. However, it can be difficult to achieve the proper trajectories of the holes so they converge within the bone. It can also be difficult and cumbersome to form the holes, which to converge are typically formed through different sides of the bone. Accessing the different sides of the bone can require different positioning of the patient and/or the surgeon, which can be awkward and time consuming. Additionally, similar to that discussed above, knotting the sutures can be difficult and tedious, particularly during laparoscopic or arthroscopic procedures.

Accordingly, there remains a need for improved methods and devices for forming bone tunnels.

SUMMARY OF THE INVENTION

The present invention generally provides methods for delivering and affixing surgical fasteners. In one embodiment, a surgical device is provided that includes a bridge member, and a shaft configured to be inserted into bone. The bridge member has proximal and distal ends with an intermediate portion extending between the proximal and distal ends. The proximal end has a proximal connector feature, the distal end has a distal connector feature, and the intermediate portion has a plurality of holes formed therethrough. The shaft can be configured to be seated in the proximal and distal connector features such that an intermediate portion of the shaft extending between the first and second ends is positioned within the bone and positioned relative to the intermediate portion of the bridge member such that respective longitudinal axes of the plurality of holes intersect a longitudinal axis of the intermediate portion of the shaft.

The shaft can have a variety of configurations. The shaft can be cannulated. The shaft can have a plurality of openings formed in the intermediate portion thereof. When the shaft is received in the proximal and distal connector features, each of the plurality of openings can be coaxially aligned with one of the plurality of holes. In some embodiments, the shaft can have at least one of a first surface feature configured to engage the proximal connector feature and a second surface feature configured to engage the distal connector feature such that when the at least of the first surface feature engages the proximal connector feature and the second surface feature engages the distal connector feature, the longitudinal axes of the plurality of holes can intersect the longitudinal axis of the intermediate portion of the shaft. When the shaft is seated in the proximal and distal connector features of the bridge member, a first end of the shaft can extend proximally beyond the proximal end of the bridge member outside the bone, and a second end of the shaft can extend distally beyond the distal end of the bridge member outside the bone.

The bridge member can also have a variety of configurations. For example, the longitudinal axes of the holes formed through the intermediate portion of the bridge member can be substantially parallel to one another. For another example, the bridge member can be u-shaped.

The proximal and distal connector features of the bridge member can vary in any number of ways. In some embodiments, at least one of the proximal and distal connector features can be keyed to the shaft such that when the shaft is received in the proximal and distal connector features, the intermediate portion of the shaft can be aligned in a predetermined orientation relative to the holes.

In another embodiment, a surgical device is provided that includes a frame having a base portion and an arm portion extending transversely from the base portion. The base portion has an opening formed therethrough, and the arm portion has a plurality of holes formed therethrough. The opening formed through the base portion can be configured to receive a surgical instrument therethrough. Each of the plurality of holes can be configured to receive a suture therethrough. A longitudinal axis of the opening formed through the base portion can be substantially perpendicular to longitudinal axes of each of the plurality of holes. The longitudinal axes of the plurality of holes can be substantially parallel to one another.

The surgical device can also include a suture capture device. The suture capture device can vary in any number of ways. The suture capture device can have at least one suture capture feature and can be configured to be advanced through the opening such that at least one suture capture feature is aligned with at least one of the holes. In some embodiments, the suture capture device can be configured to be advanced through the opening formed through the base portion to capture at least one suture extending through at least one of the plurality of holes, and retracted through the opening formed through the base portion with the at least one suture captured thereto.

In yet another embodiment, a surgical device is provided that includes a frame and a guide block. The frame has a first end, a second end, and an arcuate portion located between the first and second ends. The first end has a first bore formed therethrough that is configured to receive a first surgical instrument, and the second end has a second bore formed therethrough that is configured to receive a second surgical instrument. A longitudinal axis of the first bore can be coaxial with a longitudinal axis of the second bore. The guide block can be slidably mounted on the arcuate portion and can have a third bore formed therethrough that is configured to receive a third surgical instrument. A longitudinal axis of the third bore can intersect the longitudinal axes of the first and second bores.

The guide block can have a variety of configurations. The longitudinal axis of the third bore can intersect the longitudinal axes of the first and second bores when the guide block is at any slidable position along the arcuate portion. In some embodiments, the guide block can have one or more additional bores formed therethrough that are each configured to receive an additional surgical instrument. The longitudinal axis of the third bore can be substantially parallel to longitudinal axes of each of the one or more additional bores. The longitudinal axes of each of the one or more additional bores can intersect the longitudinal axes of the first and second bores.

The surgical device can also include a first drill guide, a second drill guide, and a probe. The first drill guide can be configured to receive a drill for drilling a bone hole, and the second drill guide can be configured to receive a drill for drilling a bone hole. The probe can have a suture coupled thereto. The first surgical instrument can include the first drill guide, the second surgical instrument can include the second drill guide, and the third surgical instrument can include the probe.

In another aspect, a surgical method is provided that includes positioning a guide device relative to bone, forming a first tunnel through the bone, forming a second tunnel in the bone by drilling through a first hole formed in the guide device, and forming a third tunnel in the bone by drilling through a second hole formed in the guide device. The second tunnel can intersect the first tunnel. The third tunnel can intersect the first tunnel and not intersect the second tunnel. In some embodiments, at least one additional tunnel can be formed in the bone. The at least one additional tunnel can intersect the first tunnel and not intersect the second tunnel or the third tunnel, and the at least one additional tunnel can be formed by drilling through at least one additional hole formed in the guide device.

The first tunnel can be formed in any number of ways. For example, forming the first tunnel can include advancing a cannulated shaft into the bone such that proximal and distal portions of the cannulated shaft extend outside the bone with an intermediate portion of the shaft extending between the first and second opposed ends being located within the bone. The guide device can have a first end mated to the proximal portion of the cannulated shaft outside the bone and can have a second end mated to the distal portion of the cannulated shaft outside the bone.

For another example, forming the first tunnel can include drilling through an opening formed in the guide device. The opening can have a longitudinal axis that is substantially perpendicular to a longitudinal axis of the first hole and to a longitudinal axis of the second hole. A first suture can be positioned to have a first portion in the first tunnel and a second portion in the second tunnel, and a second suture can be positioned to have a first portion in the first tunnel and a second portion in the third tunnel. A suture capture device can be advanced through the opening and into the first tunnel to capture the first portion of the first suture and the first portion of the second suture. The suture capture device can be removed from the first tunnel with the first portion of the first suture and the first portion of the second suture captured thereto to advance the first portion of the first suture and the first portion of the second suture through the opening.

For yet another example, forming the first tunnel can include drilling through a first bore formed in a first end of the guide device and drilling through a second bore formed in a second end the guide device. The first and second bores can have coaxial longitudinal axes. The first and second holes can be formed in an arcuate portion of the guide device located between the first and second ends. Prior to drilling through the first and second holes, a guide block having the first and second holes formed therein can be slidably positioned in a selected position along the arcuate portion.

In another embodiment, a surgical method is provided that includes forming a bone tunnel in bone, forming a first transverse tunnel in the bone, and forming a second transverse tunnel in the bone. The first transverse tunnel can intersect the bone tunnel, and the second transverse tunnel can intersect the bone tunnel. A first suture can be positioned through the anterior-posterior tunnel and through the first transverse tunnel such that a first portion of the first suture extends out of the first transverse tunnel and a second portion of the first suture extends out of the bone tunnel. A second suture can be positioned through the bone tunnel and through the second transverse tunnel such that a first portion of the second suture extends out of the second transverse tunnel and a second portion of the second suture extends out of the bone tunnel. A soft tissue can be attached to the first portion of the first suture and to the first portion of the second suture. The second portions of the plurality of sutures can be secured within the anterior-posterior tunnel. The bone tunnel can extend in an anterior-posterior direction, and the transverse tunnels can each extend in a medial-lateral direction. Positioning the first suture can include positioning the first suture to extend out of the second transverse tunnel, and positioning the second suture can include positioning the second suture to extend out of the first transverse tunnel. In some embodiments, securing the second portions of the plurality of sutures within the bone tunnel can include advancing a single fixation device into the bone tunnel.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
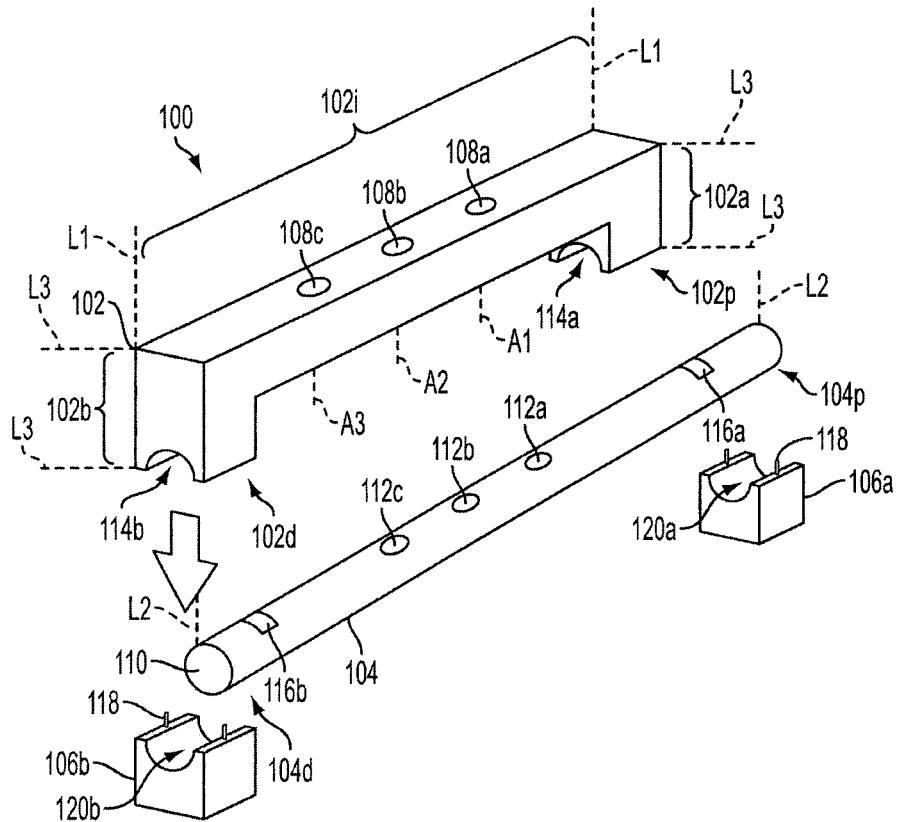
FIG. 1 is a perspective view of one embodiment of a guide device including a bridge member and an elongate shaft.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments.

Such modifications and variations are intended to be included within the scope of the present invention.

Various exemplary methods and devices are provided for forming bone tunnels. In general, the methods and devices can allow multiple converging tunnels to be formed in bone, such as in an arthroscopic surgical procedure in which tissue is secured to bone, e.g., a rotator cuff repair surgical procedure. One or more sutures can be advanced through the converging tunnels, and the suture(s) can be coupled to tissue. The suture(s) with the tissue coupled thereto can be tensioned, thereby helping to maximize an amount of the tissue in contact with the bone, which can facilitate healing. Different sutures coupled to different portions of the tissue can be advanced through different ones of the tunnels. Tensioning each of the sutures can apply forces to different portions of the tissue, which can help more surface area of the tissue contact bone. The sutures can be used to secure the tissue to the bone without using a suture anchor or other implant device, which can help reduce complexity and cost of a surgical procedure.

In an exemplary embodiment, a guide device is provided that can be configured to allow a first tunnel to be formed in bone, e.g., an anterior-posterior tunnel, and to allow a plurality of additional tunnels to be formed in the bone at predetermined angular positions relative to the first tunnel such that each of the additional tunnels can extend transverse to the first tunnel and intersect the first tunnel. The guide device can therefore allow intersecting tunnels to be formed without guesswork and without requiring any mathematical calculations to determine appropriate angular trajectories of the tunnels to ensure convergence thereof. The guide device can also be configured to advance one or more sutures through the first tunnel and the additional tunnels, which can help ease introduction of the sutures into the patient's body and/or can help ensure that the sutures pass through the correct tunnels.

The guide devices discussed herein can be used in a variety of surgical procedures in which two or more tunnels are formed in bone, such as a procedure for attaching tissue to bone, e.g., ACL repair, rotator cuff repair, etc. In an exemplary embodiment, a procedure including use of the guide device can be a minimally invasive procedure, but as will be appreciated by a person skilled in the art, the guide devices discussed herein also have application in open surgical instrumentation as well as application in robotic-assisted surgery.

The guide devices discussed herein can be formed of any one or more materials. In an exemplary embodiment, the guide device can be formed of one or more biocompatible rigid materials, e.g., stainless steel, titanium, etc.

FIG. 1 illustrates one exemplary embodiment of a guide device 100 configured to aid in securing a tissue to bone by allowing multiple bone tunnels to be formed in the bone through which one or more sutures coupled to the tissue can be advanced to secure the tissue to the bone. The guide device 100 can include a bridge member 102 and a shaft 104 configured to releasably mate with the bridge member 102. The guide device 100 can also include first and second end caps 106a, 106b configured to facilitate secure mating of the bridge member 102 and the shaft 104, as discussed further below. Generally, the bridge member 102 can have a proximal end 102p and a distal end 102d with an intermediate portion 102i extending between the proximal and distal ends 102p, 102d. The intermediate portion 102i can extend linearly between first and second legs 102a, 102b of the bridge member 102 that can extend transversely from the intermediate portion 102i. A plurality of holes 108a, 108b, 108c can be formed through the intermediate portion 102i. The shaft 104 can include an elongate member having an inner lumen 110 extending between a proximal end 104p of the shaft 104 and a distal end 104d of the shaft 104 such that the shaft 104 is cannulated. The shaft 104 can also include one or more openings 112a, 112b, 112c formed in an intermediate portion of the shaft 104 extending between the proximal and distal ends 104p, 104d. When the shaft 104 and the bridge member 102 are mated together, respective longitudinal axes A1, A2, A3 of the holes 108a, 108b, 108c can be configured to pass through the one or more openings 112a, 112b, 112c formed in the shaft 104 and to intersect the inner lumen 110. Each one of the holes 108a, 108b, 108c can therefore be configured to predictably align with one of the openings 112a, 112b, 112c. A surgical device, e.g., a drill, a suture, etc., can thus be inserted through each of the holes 108a, 108b, 108c and predictably pass through the openings 112a, 112b, 112c and extend into the inner lumen 110 of the shaft 104. In an exemplary embodiment, each of the openings 112a, 112b, 112c can be configured to coaxially align with one of the holes 108a, 108b, 108c of the bridge member 102 when the bridge member 102 is mated to the shaft 104.

As discussed further below, in use, the shaft 104 can be inserted into bone such that the proximal and distal ends 104p, 104d of the shaft 104 are positioned outside the bone and such that an intermediate portion of the shaft 104 extending between the proximal and distal ends 104p, 104d is positioned within the bone. The proximal and distal ends 102p, 102d of the bridge member 102 can be respectively mated to the proximal and distal ends 104p, 104d of the shaft 104 positioned outside the bone with the bridge member's intermediate portion 102i also being positioned outside the bone. With the bridge member 102 mated to the shaft 104, second, third, and fourth bone tunnels can be drilled into the bone respectively through the holes 108a, 108b, 108c formed through the bridge member's intermediate portion 102i and predictably pass through the openings 112a, 112b, 112c formed in the shaft 104 to extend into the inner lumen 110 of the shaft 104, thereby predictably intersecting the first bone tunnel. The intersecting bone tunnels can facilitate securing a soft tissue to the bone.

Figure 2:
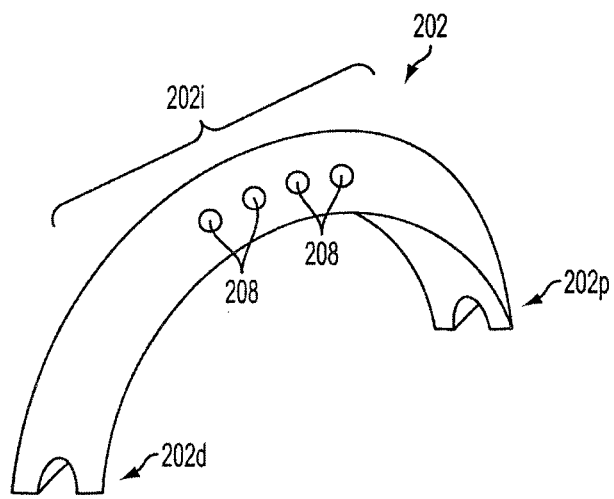
FIG. 2 is a perspective view of another embodiment of a bridge member of a guide device.

The bridge member 102 can have a variety of sizes, shapes, and configurations. The bridge member 102 can have a non-linear or non-straight shape, e.g., a u-shape. The non-linear or non-straight shape can facilitate positioning of the bridge member 102 entirely outside a patient's body by allowing the bridge member 102 to arc around the patient's body, e.g., around a joint such as a shoulder or a knee. Each of the legs 102a, 102b and the intermediate portion 102i can be linear or straight as in this illustrated embodiment such that the guide member's u-shape can be a "hard" u-shape including two right angles. In other words, each of the legs 102a, 102b can extend from the intermediate portion 102i at a right angle. Although the legs 102a, 102b are non-adjustably connected to the intermediate potion 102a in the illustrated embodiment, one or both of the legs can be adjustably connected to the intermediate portion, such as by being hingedly connected thereto. By having adjustably connected legs, a bridge member can be flattened out linearly, which can facilitate packaging and transporting the bridge member. In another embodiment, a guide device can include a bridge member having a "soft" u-shape in which the bridge member includes legs at non-right angles to an intermediate portion of the bridge member. As shown in one embodiment in FIG. 2, a bridge member 202 of a guide device can have a u-shape, but an intermediate portion 202i of the bridge member 202 including a plurality of holes 208 formed through and extending between proximal and distal ends 202p, 202d of the bridge member 202 can have a non-linear or non-straight shape, e.g., an arcuate shape, such that the bridge member has a "soft"

u-shape. The bridge member 202 includes four holes 208 in this illustrated embodiment, but a guide device can include a bridge member having any number of holes formed therethrough. In an exemplary embodiment, a bridge member can include a plurality of holes, e.g., two or more, which can facilitate securing a soft tissue to bone, as discussed further below.

Referring again to FIG. 1, the intermediate portion 102i and each of the legs 102a, 102b can have any longitudinal length. The intermediate portion 102i can have a longitudinal length L1 less than a longitudinal length L2 of the shaft 104, which can facilitate mating the proximal and distal ends 102p, 102d of the bridge member 102 to the shaft 104. In the illustrated embodiment, the longitudinal length L1 of the intermediate portion 102i defines a longitudinal length of the bridge member 102 since the legs 102a, 102b extend transversely therefrom. Each of the legs 102a, 102b can have longitudinal lengths L3 equal to one another, which can facilitate stable mating of the bridge member 102 to the shaft 104. The longitudinal lengths L3 of the legs 102a, 102b in the illustrated embodiment are less than the longitudinal length L1 of the intermediate portion 102i, but the longitudinal lengths L3 of the legs 102a, 102b can be equal to or greater than the longitudinal length L1 of the intermediate portion 102i. The longitudinal lengths L3 of the legs 102a, 102b can define a height of the bridge member 102 and hence a clearance distance between the bridge member 102 and an exterior tissue surface of a patient, e.g., a skin surface, when the shaft 104 is inserted through a patient's bone and the bridge member 102 is mated to the shaft 104 external to the patient.

The longitudinal lengths L3 of the legs 102a, 102b can be non-changeably fixed, as in the illustrated embodiment. In another embodiment, a bridge member of a guide device can include legs having variable longitudinal lengths, e.g., be configured to be telescoping, which can facilitate positioning of the bridge member relative to the patient's body. Generally, the closer that holes formed through the bridge member are to a patient's external tissue surface, the more predictably and more easily a surgical device, e.g., a drill, a suture, a suture capture device, etc., can be inserted through the holes and into the patient. In an exemplary embodiment, the bridge member used in a surgical procedure can be configured to abut an exterior tissue surface of a patient at least where holes are formed through the bridge member, e.g., at least a portion of the bridge member's intermediate portion, which can help any surgical devices inserted through the holes be directed into the patient at a predictable location with minimal displacement in any empty space between the bridge member and the exterior tissue surface. A bridge member having legs with variable longitudinal lengths can allow lengths of the legs to be increased or decreased as appropriate to abut the bridge member's intermediate portion against the patient's exterior tissue surface. Similarly, a bridge member having legs with non-changeably fixed longitudinal lengths can be selected from a plurality of bridge members each having legs with non-changeably fixed longitudinal lengths so the bridge member having legs with the most appropriate longitudinal lengths can be selected for use in a particular surgical procedure with a particular patient.

The holes 108a, 108b, 108c formed through the intermediate portion 102i can have a variety of different sizes, shapes, and configurations. Although the intermediate portion 102i includes three holes, as mentioned above, a guide device's bridge member can include any number of holes formed therethrough. In an exemplary embodiment, each of the holes 108a, 108b, 108c can be identical to one another, which can facilitate formation of identically sized and shaped bone tunnels using the holes 108a, 108b, 108c as guides, as discussed further below. The holes 108a, 108b, 108c are cylindrical with circular cross-sectional shapes in the illustrated embodiment, which can facilitate passage of a cylindrical drill guide and/or cylindrical drill therethrough. The holes 108a, 108b, 108c can, however, have other shapes.

The holes 108a, 108b, 108c can extend through the bridge member 102 such that the longitudinal axes A1, A2, A3 of the holes 108a, 108b, 108c, respectively, are substantially parallel to one another. Such arrangement of the holes 108a, 108b, 108c can allow formation of substantially parallel bone tunnels using the holes 108a, 108b, 108c as guides. Respective planes of the legs 102a, 102b can be substantially parallel to each other and to the holes' longitudinal axes A1, A2, A3, as in the illustrated embodiment where the bridge member 102 has a "hard" u-shape. The respective longitudinal axes A1, A2, A3 of the holes 108a, 108b, 108c need not be substantially parallel to one another.

The holes 108a, 108b, 108c can be located anywhere along the longitudinal length L1 of the intermediate portion 102i. In an exemplary embodiment, the holes 108a, 108b, 108c can be centered along the intermediate portion 102i. Such centered longitudinal positioning of the holes 108a, 108b, 108c can help ensure that all of the holes 108a, 108b, 108c are positioned over a patient's exterior tissue surface when the bridge member 102 is positioned relative thereto, as discussed further below. The holes 108a, 108b, 108c can also be centered latitudinally in the intermediate portion 102i, e.g., the holes 108a, 108b, 108c can be configured as cylindrical bores.

Figure 3:
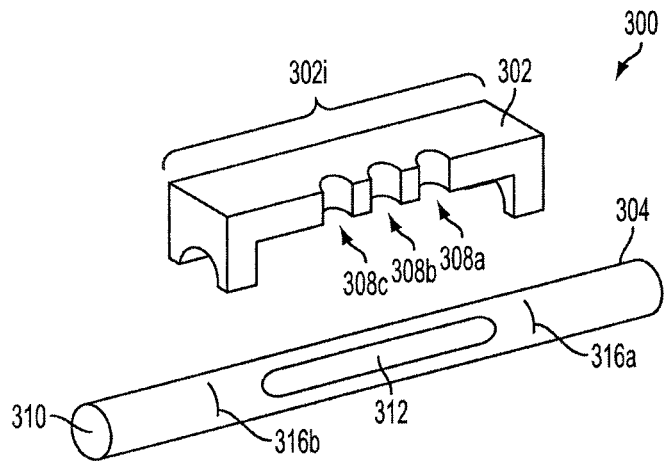
FIG. 3 is a perspective view of another embodiment of a guide device including a bridge member and an elongate shaft.
Figure 4:
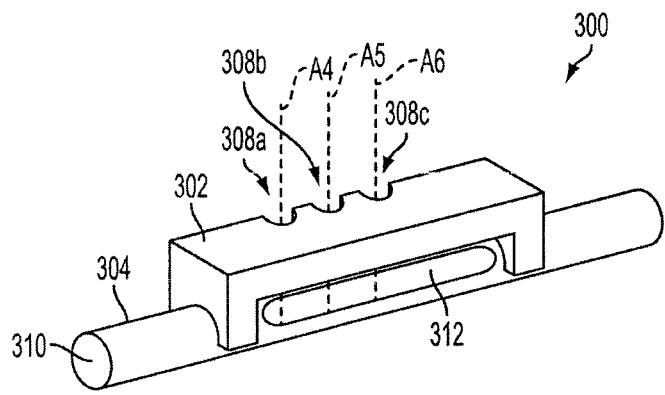
FIG. 4 is a perspective view of the guide device of FIG. 3 with the bridge member mated to the elongate shaft.

A bridge member of a guide device can include a plurality of holes that are offset longitudinally and/or latitudinally in an intermediate portion of the bridge member. FIGS. 3 and 4 illustrate another embodiment of a guide device 300 that includes a bridge member 302 having a plurality of holes 308a, 308b, 308c formed therethrough that are each offset latitudinally in an intermediate portion 302i of the bridge member 302. The holes 308a, 308b, 308c each have a semicircular cross-sectional shape. The holes 308a, 308b, 308c in the illustrated embodiments are formed through a side of the intermediate portion 302i, but a bridge member's holes can be offset latitudinally without being formed through a side of the bridge member's intermediate portion. The guide device 300 also includes shaft 304 configured to be releasably matable to the bridge member 302. When the shaft 304 and the bridge member 302 are mated together, respective longitudinal axes A4, A5, A6 of the holes 308a, 308b, 308c can be configured to pass through one or more openings 312 formed in the shaft 304 and to intersect an inner lumen 310 extending through the shaft 304.

Referring again to FIG. 1, the bridge member 102 can include one or more connector features configured to facilitate mating of the bridge member 102 to the shaft 104. The one or more connector features can help position the bridge member 102 in a predetermined orientation relative to the shaft 104, which can help ensure that the bridge member's holes 108a, 108b, 108c are automatically coaxially aligned with the shaft's openings 112a, 112b, 112c when the bridge member 102 is mated to the shaft 104. Because the shaft's openings 112a, 112b, 112c can be positioned within a patient's body when the bridge member 102 is mated to the shaft 104, and can therefore be difficult to visualize, the connector features can facilitate automatic alignment of the holes 108a, 108b, 108c with the openings 112a, 112b, 112c even without complete visualization of the openings 112a, 112b, 112c.

The connector features can have a variety of sizes, shapes, and configurations. The connector features can include cut-outs 114a, 114b formed in the bridge member 102 that can be configured to seat the shaft 104 therein. In an exemplary embodiment, the bridge member 102 can include two cut-outs 114a, 114b, one in the proximal end 102p of the bridge member 102 in the first leg 102a and another in the distal end 102d of the bridge member 102 in the second leg 102b. In this way, the cut-outs 114a, 114b can be configured to seat the shaft 104 therein when the intermediate portion of the shaft 104 is disposed within bone. The cut-outs 114a, 114b can each have a size and shape corresponding to an external size and shape of the shaft 104. In the illustrated embodiment, the cut-outs 114a, 114b each have u-shaped cross sections configured to seat the shaft 104, which is cylindrical in the illustrated embodiment. As discussed further below, at least one of the connector features can be configured to be keyed to the shaft 104 so as to align the bridge member 102 in a predetermined orientation relative to the shaft 104 when the connector features engage the shaft 104.

In addition or in alternative to the cut-outs 114a, 114b, the bridge member 102 can include connector features in the form of visual marks, e.g., lines, colors, lights, symbols, etc., and/or tactile marks, e.g., grooves, etc., configured to align with corresponding surface feature(s) of the shaft 104, as discussed further below.

The shaft 104 can have a variety of sizes, shapes, and configurations. The shaft 104 can have a cylindrical shape and can have a circular cross-sectional shape, which can facilitate formation of a cylindrical bone tunnel using the shaft 104 and/or insertion of the shaft 104 into a cylindrical bone tunnel. The shaft 104 can have any longitudinal length L2, but as mentioned above, in an exemplary embodiment, the shaft's longitudinal length L2 can be greater than the longitudinal length L1 of the intermediate portion 102i. The shaft 104 in the illustrated embodiment is cannulated, but a shaft can be partially cannulated, such as by having a solid or closed proximal end.

The openings 112a, 112b, 112c formed through the shaft 104 can have a variety of different sizes, shapes, and configurations. Although the shaft 104 includes three openings, as mentioned above, a guide device's shaft can include any number of openings formed therethrough. The number of openings 112a, 112b, 112c can equal a number of holes 108a, 108b, 108c formed through the bridge member 102, as in the illustrated embodiment, or the numbers of openings 112a, 112b, 112c and holes 108a, 108b, 108c can differ. FIGS. 3 and 4 illustrate an embodiment of a shaft 304 including a single opening 312. The longitudinal axes A3, A4, A5 of the holes 308a, 308b, 308c of the bridge member 302 can each pass through the opening 312 when the bridge member 302 is mated to the shaft 304, as shown in FIG. 4.

Referring again to FIG. 1, in an exemplary embodiment, each of the openings 112a, 112b, 112c can be identical to one another, which can facilitate formation of identically sized and shaped bone tunnels using the openings 112a, 112b, 112c as guides, as discussed further below. The openings 112a, 112b, 112c have circular cross-sectional shapes in the illustrated embodiment, which can facilitate passage of a cylindrical drill guide and/or cylindrical drill therethrough. The openings 112a, 112b, 112c can, however, have other shapes. The openings 112a, 112b, 112c can extend all the way through the shaft 104 or, as in the illustrated embodiment, the openings 112a, 112b, 112c can be formed through one side of the shaft 104. In this way, a surgical device inserted into the inner lumen 110 through any of the openings 112a, 112b, 112c can be less likely to pass out of the inner lumen 110 until and if the device is intentionally removed therefrom.

As mentioned above, the shaft 104 can include one or more surface features configured to align with corresponding connector features of the bridge member 102. The one or more surface features can have a variety of sizes, shapes, and configurations. The one or more surface features can be in the form of visual marks, e.g., lines, colors, lights, symbols, etc., and/or tactile marks, e.g., grooves, etc., configured to align with corresponding connector feature(s) of the bridge member 102. Additionally or alternatively, the one or more surfaces features can include tracks 116a, 116b formed in an external surface of the shaft 104 that are configured to engage the connector features of the bridge member 102, e.g., engage the cut-outs 114a, 114b. The tracks 116a, 116b can generally include depressions or scores formed in the shaft 104. The tracks 116a, 116b can have a size and shape corresponding to a size and shape of the cut-outs 114a, 114b and can extend around a partial perimeter or circumference of the shaft's external surface. The tracks 116a, 116b can therefore be keyed to the cut-outs 114a, 114b such that when the cut-outs 114a, 114b engage the tracks 116a, 116b, the bridge member 102 can be aligned in a predetermined orientation relative to the shaft 104. Although all of the tracks 116a, 116b are keyed to the cut-outs 114a, 114b in the illustrated embodiment, a bridge member can have any one or more of its connector features keyed to a shaft matable to the bridge member. In another embodiment, tracks can extend entirely around a perimeter or circumference of a shaft's external surface. A bridge member can nevertheless be configured to mate to the shaft in a predetermined orientation relative thereto via one or more additional surface features and connector features configured to indicate alignment of the bridge member relative to the shaft, such as by aligning corresponding symbols, e.g., dots, formed on the bridge member and the shaft with the bridge member engaging the shaft's tracks. FIGS. 3 and 4 illustrate an embodiment of a shaft 304 including surface features 316a, 316b in the form of colored lines formed on an external surface of the shaft 304 around a partial perimeter or circumference of the shaft 304. The surface features 316a, 316b can indicate where connector features 314a, 314b of the bridge member 302 can contact the shaft 304 so as to align the holes 308a, 308b, 308c with the opening 312.

Referring again to FIG. 1, as mentioned above, the first and second end caps 106a, 106b can be configured to facilitate secure mating of the bridge member 102 and the shaft 104, which can help reduce movement of the bridge member 102 along the longitudinal length L2 of the shaft 104 when the bridge member 102 and the shaft 104 are mated together. Such reduction of movement can facilitate predictable insertion of surgical devices through the holes 108a, 108b, 108c and into the inner lumen 110. In other words, the end caps 106b, 106c can be configured to help maintain coaxial alignment of the holes 108a, 108b, 108c with the openings 112a, 112b, 112c.

Figure 7:
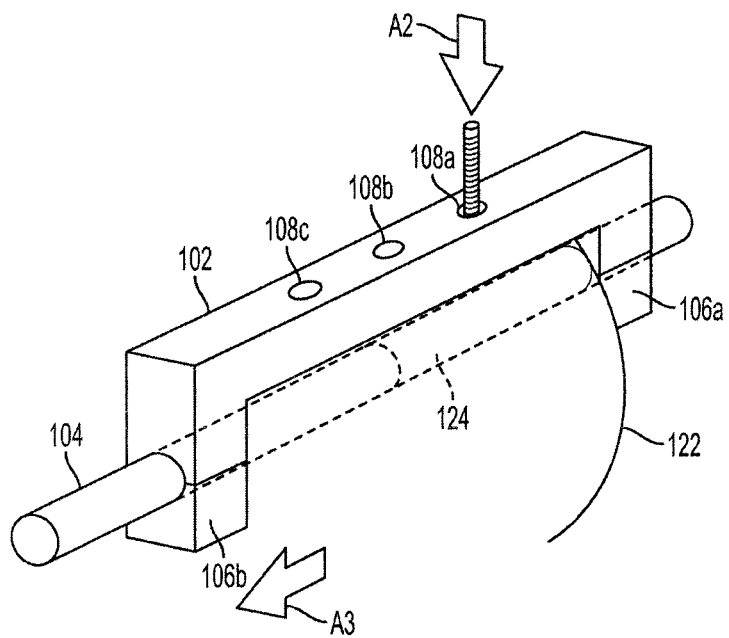
FIG. 7 is a perspective view of the elongate shaft mated to the bridge member of FIG. 6, a drill being advanced through a hole formed in the bridge member and into the bone.

The first and second end caps 106a, 106b can be configured to mate to the bridge member's first and second legs 102a, 102b, respectively, so as to sandwich or position the shaft 104 therebetween, as shown in FIG. 7 and as discussed further below. The end caps 106a, 106b can have a variety of sizes, shapes, and configurations. The end caps 106a, 106b can each include a cut-out 120a, 120b formed therein that can be configured to seat the shaft 104 therein, e.g., an opposite side of the shaft 104 from that seated in the cut-outs 114a, 114b of the bridge member 102. The cut-outs 120a, 120b can each have a size and shape corresponding to the external size and shape of the shaft 104. In the illustrated embodiment, the cut-outs 120a, 120b each have u-shaped cross sections configured to seat the shaft 104, which is cylindrical in the illustrated embodiment.

The first and second end caps 106a, 106b can be configured to mate to the bridge member 102 in a variety of ways, e.g., snap fit, compression fit, magnets, etc. The first and second end caps 106a, 106b in the illustrated embodiment each include at least one male member or protrusion 118 configured to be received in a corresponding female member or depression (not shown) formed in the bridge member 102, e.g., formed in the first and second legs 102a, 102b adjacent the cut-outs 114a, 114b, so as to mate the end caps 106a, 106b to the bridge member 102 by compression fit.

A guide device kit can be provided including one or more cannulated shafts and one or more bridge members each configured to releasably mate to at least one of the cannulated shafts. The kit can optionally include one or more end caps configured to mate with one or more of the bridge members to help secure a cannulated shaft thereto. Each of the shafts can have a different size, different shape, and/or different configuration than the other shafts, and each of the bridge members can have a different size, different shape, and/or different configuration than the other bridge members. In this way, the bridge member having the most appropriate size, shape, and configuration, and the shaft having the most appropriate size, shape, and configuration, can be selected for use in a particular surgical procedure with a particular patient, which can help a single kit accommodate various graft sizes, different surgical procedures, and different patient anatomies. The guide device kit can include one or more additional surgical tools configured to be used with a guide device, e.g., one or more sutures, one or more drills, one or more drill guides, etc.

In use, as mentioned above, the guide devices disclosed herein can be used in a minimally invasive surgical procedure for securing a ligament graft to bone. Generally, the patient can first be prepared for the surgery using standard techniques. A suitable graft can be provided, for example, through harvesting a semitendinosus graft from the patient, or by providing an allograft, although any type and source of graft can be implanted using the methods of this invention, including soft tissue grafts and grafts terminated with bone blocks or substitute rigid materials.

FIGS. 5-9 illustrate an exemplary embodiment of a surgical procedure for tunnel repair. Although the procedure is illustrated with respect to the guide device 100 of FIG. 1, any of the guide devices disclosed herein can be similarly used. Also, although the procedure is illustrated with respect to a rotator cuff repair at a shoulder, any of the guide devices disclosed herein can be used at a variety of anatomical locations to repair various tissue problems.

Figure 5:
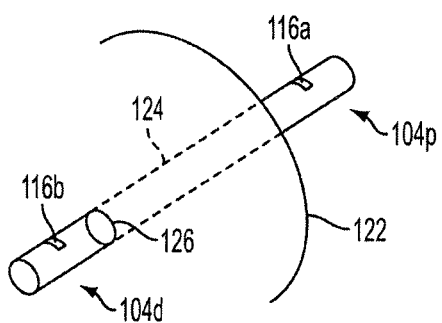
FIG. 5 is a perspective view of the elongate shaft of FIG. 1 inserted through a bone.

As shown in FIG. 5, a first bone tunnel, cross tunnel, horizontal tunnel, or anterior-posterior tunnel 124, generally referred to herein as a "first bone tunnel," can be formed in a bone 122 of a patient, e.g., a shoulder bone. The first bone tunnel 124 can be formed in the bone 122 in a variety of ways, as will be appreciated by a person skilled in the art, such as by drilling with a drill through an anterior portal 126 on an anterior side of the bone 122 and out a posterior portal (not shown) on a posterior side of the bone 122. The first bone tunnel 124 can have any size and shape. In an exemplary embodiment, the first bone tunnel 124 can have a cylindrical shape and a circular cross-section, although the first bone tunnel 124 can have other shapes. The first bone tunnel 124 can have a maximum diameter in an exemplary embodiment of less than about 5 mm, e.g., about 4 mm or about 3 mm. The shaft 104 can be advanced into the first bone tunnel 124 as the first bone tunnel 124 is being formed, or the shaft 104 can be advanced therein after the first bone tunnel 124 has been formed. One or more sutures (not shown) can be positioned within the inner lumen 110 of the shaft 104 when the shaft 104 is advanced into the bone 122.

The shaft 104 can be positioned within the first bone tunnel 124 with the proximal and distal ends 104p, 104d of the shaft 104 located outside the bone 122 and with the intermediate portion of the shaft 104 positioned within the bone 122, as shown in FIG. 5. In particular, the proximal end 104p of the shaft 104 can be located outside the bone 122 on the posterior side of the bone 122, and the distal end 104d of the shaft 104 can be located outside the bone 122 on the anterior side of the bone 122. If the shaft 104 includes surface features, e.g., the tracks 116a, 116b, the surface features can also be located outside the bone 122, which can facilitate mating of the bridge member 102 to the shaft 104.

Figure 6:
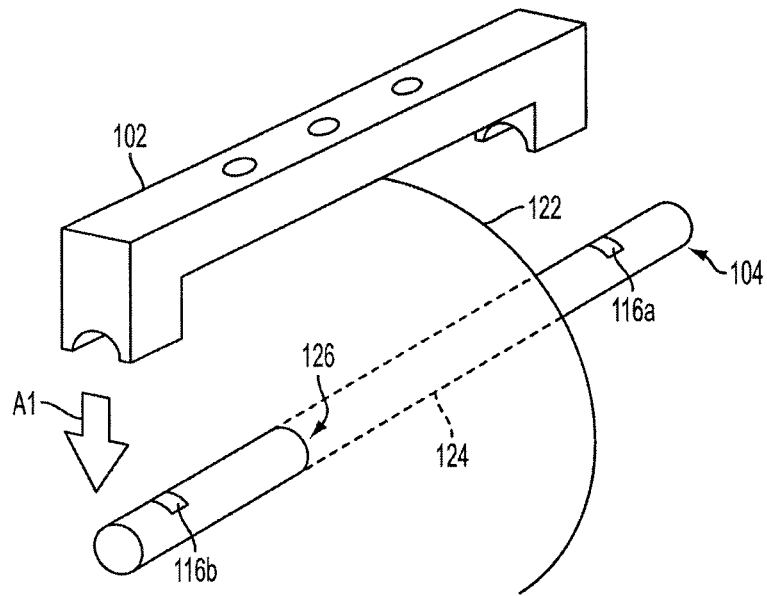
FIG. 6 is a perspective view of the elongate shaft of FIG. 5 with the bridge member of FIG. 1 being advanced toward the elongate shaft.

As shown in FIG. 6, when the shaft 104 extends through the bone 122, the bridge member 102 can be advanced in a direction indicated by arrow A1 into mating engagement with the shaft 104. The shaft 104 can be seated in the cut-outs 114a, 114b, with the bridge member 102 engaging the tracks 116a, 116a. The shaft 104 can be rotated about a longitudinal axis thereof within the first bone tunnel 124 before and/or after the bridge member 102 is mated to the shaft 104 to position the tracks 116a, 116b at a selected position relative to the bone 122 so the bridge member 102 when mated to the shaft 104 can be at a desired position relative to the bone 122. Additionally or alternatively, after the bridge member 102 has been mated to the shaft 104, the bridge member 102 can be rotated about the longitudinal axis of the shaft 104 to position the bridge member 102 at a selected position relative to the bone 122. The end caps 106a, 106b can be mated to the bridge member 102 after the shaft 104 has engaged the bridge member 102, e.g., after the shaft 104 has been seated in the cut-outs 114a, 114b. The bridge member 102 can be rotated about the longitudinal axis of the shaft 104 before and/or after the end caps 106a, 106b are mated to the bridge member 102. The shaft 104 can rotate with the bridge member 102 such that the longitudinal axes A1, A2, A3 of the holes 108a, 108b, 108c can remain coaxial with longitudinal axes of the shaft's openings 112a, 112b, 112c as the bridge member 102 rotates. The tracks 116a, 116b, as well as the end caps 106a, 106b, can be configured to help maintain the bridge member 102 and the shaft 104 in such a predetermined orientation relative to one another with the respective axes of the holes 108a, 108b 108c and openings 112a, 112b, 112c being coaxial. FIG. 7 illustrates the bridge member 102 mated to the shaft 104, the end caps 106a, 106b mated to the bridge member 102, and a distal surface of the intermediate portion 102i abutting an external tissue surface of the patient. As in the illustrated embodiment, when the shaft 104 is seated in the proximal and distal connector features of the bridge member 102, the proximal end of the shaft 104p can extend proximally beyond the proximal end 102p of the bridge member 102 outside the bone 122, and the distal end 104d of the shaft 104 can extend distally beyond the distal end 102d of the bridge member 102 outside the bone 122. In another exemplary embodiment, a shaft can be configured to mate to a bridge member such that proximal and distal ends of the shaft do not extend proximally beyond a proximal end of the bridge member or distally beyond a distal end of the bridge member.

Figure 8:
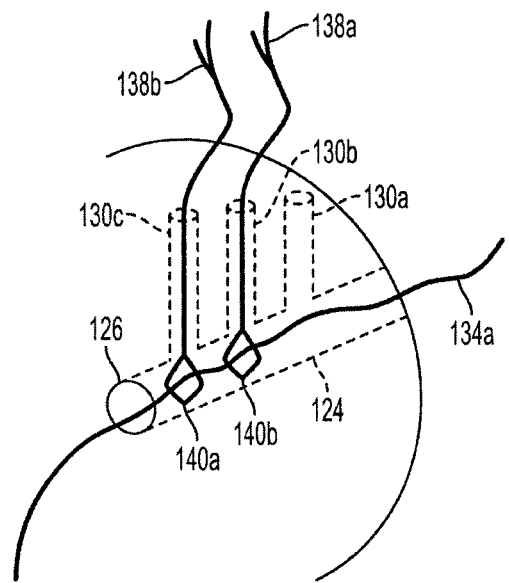
FIG. 8 is a perspective view of the bone of FIG. 7 with a suture and two chias positioned in tunnels formed therein.

One or more additional bone tunnels or transverse tunnels can be formed in the bone 122 of a patient using one or more of the holes 108a, 108b, 108c of the guide device 100 as guides. In an exemplary embodiment, an additional bone tunnel can be formed using each of the holes 108a, 108b, 108c such that a number of additional bone tunnels equals a number of the holes 108a, 108b, 108c. Because the longitudinal axes A1, A2, A3 of the holes 108a, 108b, 108c can be coaxial with the longitudinal axes of the shaft's openings 112a, 112b, 112c when the bridge member 102 is mated to the shaft 104, the additional bone tunnel(s) can each predictably intersect the first bone tunnel 124. The additional bone tunnel(s) can be formed in any way, such as by advancing a drill 128 sequentially through each of the holes 108a, 108b, 108c in a direction shown by arrow A2 in FIG. 7. The additional bone tunnel(s) can each have any size and shape. In an exemplary embodiment, the each of the additional bone tunnel(s) can have a cylindrical shape and a circular cross-section, although the additional bone tunnel(s) can have other shapes. The additional bone tunnel(s) can each have a maximum diameter in an exemplary embodiment of less than about 2 mm, e.g., about 1.5 mm. Although the drill 128 is shown being first advanced through the first hole 108a, the additional bone tunnel(s) can be formed using any of the holes 108a, 108b, 108c as guides and can be formed therethrough in any order. Because the openings 112a, 112b, 112c can be aligned with the holes 108a, 108b, 108c, the drill 128 can advance through a one of the holes 108a, 108b, 108c, through the external tissue surface, into the bone 124, and through an associated one of the openings 112a, 112b, 112c such that the additional bone tunnel formed by the drill 128 extends from outside the patient's body into the first bone tunnel 124. The openings 112a, 112b, 112c can help ensure that the additional bone tunnel(s) are drilled along the coaxial axes such that each of the additional bone tunnel(s) can be substantially parallel to one another and transverse to the first bone tunnel 124. Although, as mentioned above, the respective axes A1, A2, A3 of the holes 108a, 108b, 108c, and hence the respective longitudinal axes of the openings 112a, 112b, 112c, need not be substantially parallel to one another, though in an exemplary embodiment, the respective axes A1, A2, A3 of the holes 108a, 108b, 108c can be aligned such that bone tunnels formed through the holes 108a, 108b, 108c each intersect the first bone tunnel 124 without intersecting one another. The presence of the first bone tunnel 124 in the bone 122 can indicate by feel when each of the additional bone tunnels 130a, 130b, 130c should stop being drilled, and/or an interior surface of the shaft 104 can help prevent the drill 128 from drilling past the first bone tunnel 124. Additionally or alternatively, the shaft 104 can be visualized, e.g., with a scoping device inserted into the patient, to help prevent overdrilling of the additional bone tunnel(s). Second, third, and fourth bone tunnels 130a, 130b, 130c formed using each of the holes 108a, 108b, 108c as guides, respectively, are shown in FIG. 8.

After the second, third, and fourth bone tunnels 130a, 130b, 130c have been formed in the bone 122, the bridge member 102 can be rotated about the longitudinal axis of the shaft 104 to position the bridge member 102 at a different position relative to the bone 122. One or more additional bone tunnels can be formed using the holes 108a, 108b, 108c as guides with the bridge member 102 in this secondary location relative to the bone 122. These one or more additional bone tunnels can be substantially parallel to one another, transverse to the first bone tunnel 124, and with longitudinal axes thereof intersecting the longitudinal axes of the previously formed additional tunnels 130a, 130b, 130c, although the additional tunnels need not be substantially parallel to one another. The one or more additional tunnels can allow a same tissue secured to the bone using the previously formed additional tunnels 130a, 130b, 130c to be tensioned and secured to the bone 122 from different angles than the previously formed additional tunnels 130a, 130b, 130c, which can provide redundancy in case of suture failure and can help urge the tissue into greater contact with the bone 122, which can facilitate healing and can help keep the tissue in greater contact with the bone 122 as the patient moves.

At least one suture can be positioned within the first bone tunnel 124 and at least one of the additional bone tunnels 130a, 130b, 130c. As mentioned above, at least one suture can be positioned in the shaft 104 when the shaft 104 is advanced into the bone 122. In an exemplary embodiment, at least one suture can be advanced into the first bone tunnel 124 after the shaft 104 has been inserted into the bone 122 and removed therefrom after the additional bone tunnels 130a, 130b, 130c have been formed. In other words, the at least one suture can be positioned directly within the first bone tunnel 124. The shaft 104 can be removed from the bone 122 by advancing the shaft 104 in an anterior direction, as shown by arrow A3 in FIG. 7, and out of the anterior portal 126. The shaft 104 instead be advanced in a posterior direction and out of the posterior portal.

Figure 10:
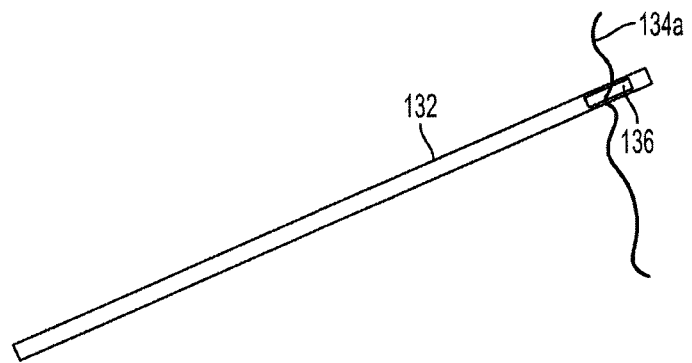
FIG. 10 is a side view of one embodiment of a guide pin.

The at least one suture can be positioned in the first bone tunnel 124 in a variety of ways, as will be appreciated by a person skilled in the art. In an exemplary embodiment, the at least one suture can be coupled to a suture placement device and advanced into the first bone tunnel 124. FIG. 10 illustrates one embodiment of a suture placement device in the form of a guide pin 132. The guide pin 132 can generally be a rigid elongate member configured to be advanced into a patient's body. A first suture 134a can be coupled to the guide pin 132 by, e.g., passing through an eyelet 136 formed through a distal end of the guide pin 132. A proximal end of the guide pin 132 can be advanced into the first bone tunnel 124, e.g., through the anterior portal 126 and advanced therethrough, trailing the first suture 134a at the distal end of the guide pin 132 so as to advance the first suture 134a into the first bone tunnel 124 as the distal end of the guide pin 132 advanced through the first bone tunnel 124 and out the bone 122 through the posterior portal. The first suture 134a is shown extending through the first bone tunnel 124 in FIG. 8 after the guide pin 132 has been detached from the first suture 134a, e.g., by cutting the first suture 134a. The first suture 134a is shown as a single, unfolded strand of suture, but the first suture 134a can include multiple sutures and/or or a folded suture.

Figure 9:
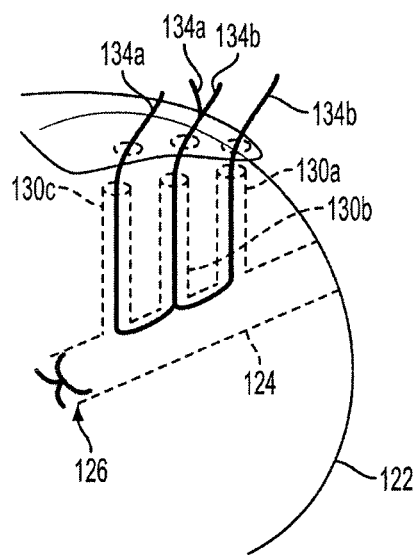
FIG. 9 is a perspective view of the bone of FIG. 8 with the suture having portions positioned in three of the tunnels and with another suture having portions positioned in three of the tunnels.

Prior to advancing the first suture 134a into the first bone tunnel 124, at least one suture capture device can be advanced into the first bone tunnel 124 so as to capture the first suture 134a when the first suture 134a passes through the first bone tunnel 124. The suture capture device can have a variety of configurations. In an exemplary embodiment, the suture capture device can include a chia, such as the Chia Percpasser™ available from Depuy Mitek, Inc. of Raynham, Mass. Generally, a chia can be configured similar to a needle and include a thin elongate member having an eyelet or kite at one end thereof through which at least one suture can pass. The chia can be formed of a variety of materials, e.g., stainless steel, a shape memory material such as Nitinol, etc. In an exemplary embodiment, as shown in FIG. 8, first and second chias 138a, 138b can be advanced through the third and fourth bone tunnels 130b, 130c, respectively, prior to the first suture 134a being advanced into the first bone tunnel 124. In this way, when the first suture 134a is advanced into the first bone tunnel 124, the first suture 134a can pass through kites 140a, 140b at ends of the chias 138a, 138b so as to be captured by the chias 138a, 138b, as shown in FIG. 9.

Figure 11:
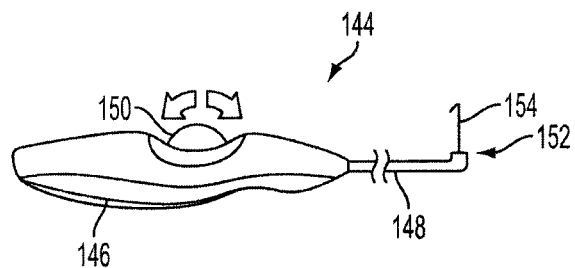
FIG. 11 is a side view of one embodiment of a suture capture device.
Figure 12:
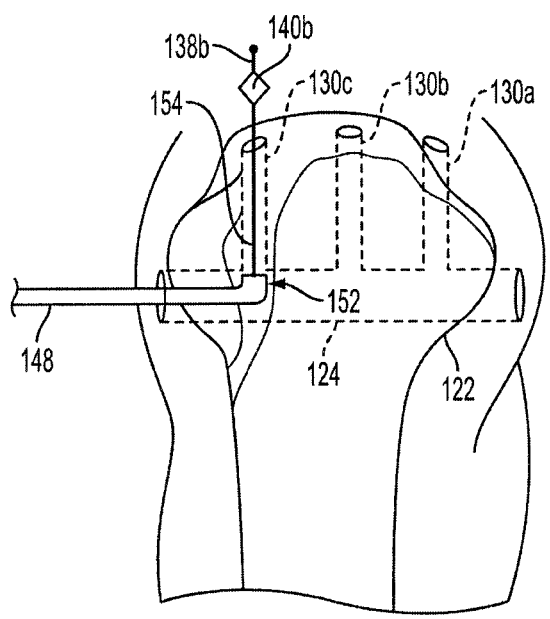
FIG. 12 is a side view of a distal portion of the suture capture device of FIG. 11 inserted into a bone tunnel formed in a bone and capturing a chia positioned in another bone tunnel formed in the bone.

FIG. 11 illustrates an embodiment of a suture capture device 144 configured to advance the chias 138a, 138b into the bone 122. The device 144 can include a handle 146 having a cannulated elongate shaft 148 extending therefrom. The handle 146 can include an actuator, e.g., a thumbwheel 150, configured to be actuated to move a grasper wire 154 in and out a distal end 152 of the elongate shaft 148. The grasper wire 154 can have a hook at a distal tip thereof that can be configured to "hook" an eyelet such as a chia's kite. The actuator is illustrated as a thumbwheel 150 in this embodiment, but the actuator can have other configurations, e.g., a button, a lever, a knob, am electric switch, etc. The distal end 152 can have be angled at about 90 degrees from a remainder of the elongate shaft 148, which can allow the device 144 to advance the grasper wire 154 in and out of a bone tunnel, e.g., one of the bone tunnels 130a, 130b, 130c, that is substantially perpendicular to a bone tunnel in which the elongate shaft 148 primarily extends, e.g., the first bone tunnel 124. The grasper wire 154 can be flexible so as to allow the grasper wire 154 to bend at the substantially 90 degree angle at the shaft's distal end 152. FIG. 12 shows the elongate shaft 148 extending primarily through the first bon tunnel 124 with the distal end 152 thereof angled to allow the grasper wire 154 to exit the elongate shaft 148 and enter the fourth bone tunnel 130c. FIG. 12 also shows the grasper wire 154 extending through the fourth bone tunnel 130c and grasping the second chia 138b. The thumbwheel 150 can be further actuated to advance the grasper wire 154 and the second chia 138b toward the first bone tunnel 124 to position the kite 140b therein.

With the first suture 134a captured by the chias 138a, 138b, the chias 138a, 138b can be retracted from the second and third bone tunnels 130b, 130c, respectively, to pull the first suture 134a therethrough. The first suture 134a can therefore be positioned within the first bone tunnel 124 and within two of the additional bone tunnels. As shown in FIG. 9, a first portion of the first suture 134a can extend through the third bone tunnel 130b, a second portion of the first suture 134a can extend through the fourth bone tunnel 130c, and an intermediate portion of the first suture 134a extending between the first and second portions can extend through the first bone tunnel 124. A second suture 134b can be similarly positioned to extend through the first bone tunnel 124, the second bone tunnel 130a and the third bone tunnel 130b. Each of the sutures 134a, 134b in the illustrated embodiment extend through adjacent additional bone tunnels, e.g., the third and fourth tunnels 130b, 130c for the first suture 134a and the second and third tunnels 130a, 130b for the second suture 134b, but a suture can be advanced through non-adjacent additional bone tunnels, e.g., the second tunnel 130a and the fourth tunnel 130c. The additional tunnels through which a suture extends can depend on one or more factors such as patient anatomy, a total number of sutures, where a tissue coupled to the suture is intended to be secured to the bone 122, etc. In an exemplary embodiment, a number of sutures positioned in the first bone tunnel 124 can be one equal to or less than a number of additional bone tunnels, e.g., two sutures 134a, 134b in this illustrated embodiment including three additional bone tunnels 130a, 130b, 130c. The sutures 134a, 134b can be color-coded or otherwise marked for unique identification, which can help identify the sutures 134a, 134b for tensioning and tissue securing purposes. The unique marking can also help ensure that each of the sutures 134a, 134b has properly passed through the bone tunnels.

One or more tissues (not shown) can be attached to each of the sutures 134a, 134b, e.g., by whip stitch, by knotting, etc. The sutures 134a, 134b can be tensioned, e.g., pulled, to urge the tissue into contact with the bone 122, and can be thereafter secured, e.g., by knotting. The sutures 134a, 134b can be individually tensioned, which can allow different portions of the tissue to which the different sutures 134a, 134b are attached to be tensioned and brought into close contact with the bone 122. The anterior portal 126 and the posterior portal can be closed for healing, such as by being sewn or sutured shut as shown in FIG. 9. The anterior portal 126 and the posterior portal can be closed at any point after the shaft 104 had been removed from the first bone tunnel 124 and the sutures 134a, 134b have been positioned in the first bone tunnel 124. In an exemplary embodiment, the anterior portal 126 and the posterior portal can be closed after the tissue has been secured to the bone, which can facilitate adjustment and/or replacement of the sutures 134a, 134b and/or adding one or more additional sutures, before the tissue is secured in place.

Figure 13:
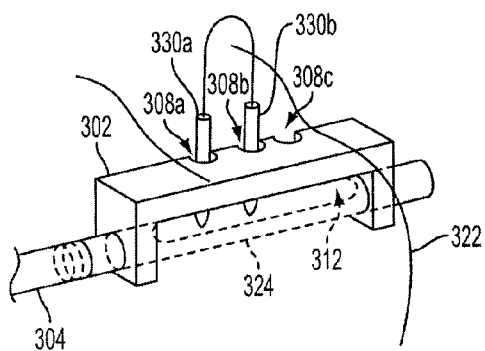
FIG. 13 is a perspective view of the guide device of FIG. 4 with the elongate shaft positioned in a bone and with a suture coupled to the bridge member and extending through bone tunnels formed in the bone.
Figure 14:
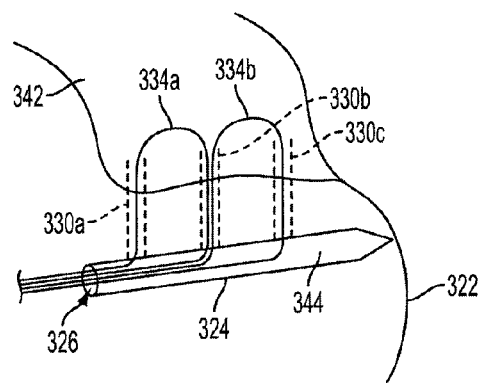
FIG. 14 is a side view of the suture of FIG. 13 and another suture secured in the bone with a fixation device.

The procedure illustrated in FIGS. 5-9 involves knotted tunnel repair in which the one or more sutures used to secure tissue to bone can be knotted to so secure the tissue. FIGS. 13 and 14 illustrate an embodiment of a surgical procedure for knotless tunnel repair. Although the procedure is illustrated with respect to the guide device 300 of FIGS. 3 and 4, any of the guide devices disclosed herein can be similarly used. Also, although the procedure is illustrated with respect to a rotator cuff repair at a shoulder, any of the guide devices disclosed herein can be similarly used in another type of procedure.

The procedure of FIGS. 13 and 14 can generally be similar to the procedure of FIGS. 5-9. A first bone tunnel 324 can be formed in a bone 322 of a patient. A plurality of additional bone tunnels 330a, 330b, 330c can be formed in the bone 322 to intersect the first bone tunnel 324 using the holes 308a, 308b, 308c of the bridge member 302 as guides. As shown in FIG. 13, a first suture 334a can be positioned in the second bone tunnel 330a and the third bone tunnel 330b such that a first portion of the first suture 334a can extend through the second bone tunnel 330a, a second portion of the first suture 334a can extend through the third bone tunnel 330b, and an intermediate portion of the first suture 334a extending between the first and second portions can be positioned outside the bone 322 and extend between the second and third tunnels 330a, 330b. Ends of the first suture 334a can be positioned within the first bone tunnel 324. The ends of the first suture 334a within the first bone tunnel 324 can be captured using a suture capture device, e.g., a hook, a grasper, etc., advanced anteriorly through an anterior portal 326 into the first bone tunnel 324, and advanced out of the first bone tunnel 324 by removing the suture capture device form the first bone tunnel 324 with the suture 334a captured thereto, e.g., by removing the suture capture device from the anterior portal 326 through which is was inserted. The ends of the first suture 334a can thus be pulled out of the first bone tunnel 324, and the first suture 334a can be tensioned and secured to secure to the bone 322 a tissue 342 attached to the intermediate portion of the first suture 334a, as shown in FIG. 14.

A second suture 334b can be similarly positioned in the third bone tunnel 330b and the fourth bone tunnel 330c such that a first portion of the second suture 334b can extend through the third bone tunnel 330b, a second portion of the second suture 334b can extend through the fourth bone tunnel 330c, and an intermediate portion of the second suture 334b extending between the first and second portions can be positioned outside the bone 322 and extend between the third and fourth tunnels 330b, 330c. The ends of the second suture 334b can be pulled out of the first bone tunnel 324, and the second suture 334b can be tensioned and secured to secure to the bone 322 the tissue 342 attached to the intermediate portion of the second suture 334b, as shown in FIG. 14. Similar to that mentioned above, the first and second sutures 334a, 334b can be color-coded or otherwise uniquely identified.

The first and second sutures 334a, 334b can be secured within the first bone tunnel 324 to secure the tissue 342 to the bone 322. The first and second sutures 334a, 334b can be secured in a variety of ways. In an exemplary embodiment, a single fixation device 344 can be advanced into the first bone tunnel 324 to secure the sutures 334a, 334b. Although the fixation device is illustrated as a pin 344 in FIG. 14, the fixation device can have a variety of configurations, e.g., a screw, a suture anchor, cement, a pin, etc. Securing a plurality of sutures 334a, 334b with a single fixation device can reduce an amount of hardware implanted in a patient, which can reduce infection risk, can save time and effort during a surgical procedure because each of the sutures 334a, 334b need not be individually attended to for securing, and because the sutures 334a, 334b need not be knotted, which can be time-consuming and cumbersome.

Figure 15:
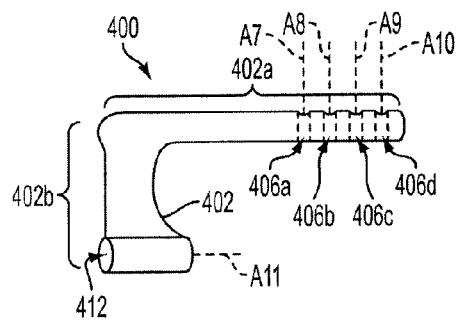
FIG. 15 is a side view of one embodiment of a guide device including an L-shaped frame.
Figure 16:
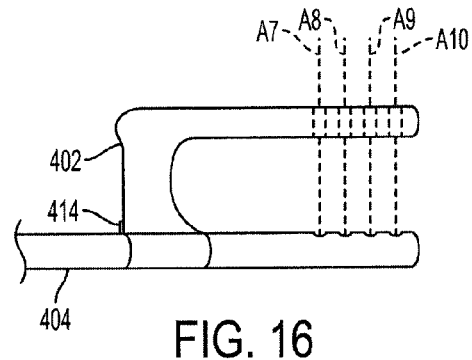
FIG. 16 is a side view of the guide device of FIG. 15 having an elongate shaft advanced through an opening formed therethrough.
Figure 17:
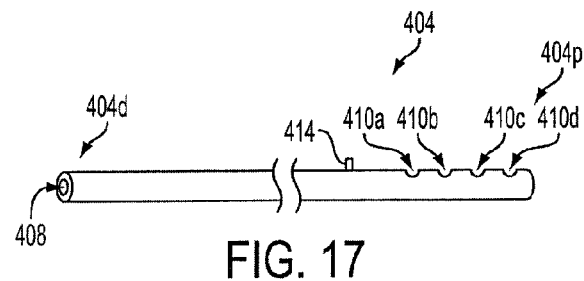
FIG. 17 is a side view of the elongate shaft of FIG. 16.

FIGS. 15 and 16 illustrate another exemplary embodiment of a guide device 400 configured to aid in securing a tissue to bone by allowing multiple bone tunnels to be formed in the bone through which one or more sutures coupled to the tissue can be advanced to secure the tissue to the bone. The guide device 400 can include a frame 402 including a base portion 402b and an arm portion 402a extending transversely from the base portion 402b. The base portion 402b can have an opening 412 formed therethrough configured to slidably receive a surgical instrument such as a cannulated shaft 404, shown in FIGS. 16 and 17 and discussed further below.

The arm portion 402a of the frame 402 can have a plurality of holes 406a, 406b, 406c, 406d formed therethrough. Although the arm portion 402a of the frame 402 includes four holes 406a, 406b, 406c, 406d in the illustrated embodiment, an arm portion of a frame can include any number of holes, similar to that discussed above regarding holes of a guide device's bridge member. The holes 406a, 406b, 406c, 406d can be located anywhere along a longitudinal length of the arm portion 402a, although in an exemplary embodiment they can be located adjacent a free terminal end thereof. In an exemplary embodiment, the holes 406a, 406b, 406c, 406d can be centered along the arm portion 402a. Also similar to that discussed above regarding the holes of a guide device's bridge member, respective longitudinal axes a7, a8, a9, a10 of the frame's holes 406a, 406b, 406c, 406d can be substantially parallel to one another, and the holes 406a, 406b, 406c, 406d can have any size and shape and can be centered or offset latitudinally in the arm portion 402a. In another embodiment, the respective longitudinal axes a7, a8, a9, a10 of the frame's holes 406a, 406b, 406c, 406d need not be substantially parallel to one another, also similar to that discussed above. In the illustrated embodiment, the holes 406a, 406b, 406c, 406d are centered latitudinally in the arm portion 402a and are configured as cylindrical bores. A longitudinal axis a11 of the frame's opening 412 can be substantially perpendicular to the respective longitudinal axes a7, a8, a9, a10 of the frame's holes 406a, 406b, 406c, 406d, which can facilitate capture of sutures extending through the holes 406a, 406b, 406c, 406d as discussed further below.

The base and arm portions 402b, 402a can each have any longitudinal length. A longitudinal length of the base portion 402b can define a height of the guide device 400 and hence a clearance distance between the arm portion 402a and an exterior tissue surface, e.g., a skin surface, when the guide device 400 is positioned outside a patient's body, as discussed further below. The longitudinal length of the base portion 402b can be non-changeably fixed, as in the illustrated embodiment. In another embodiment, a base portion of a guide device can have a variable longitudinal length, e.g., be configured to be telescoping, which can facilitate positioning of the guide device's arm portion relative to the patient's body, similar to that discussed above regarding the bridge member.

The shaft 404 can include an elongate member having an inner lumen 408 extending between a proximal end 404p of the shaft 404 and a distal end 404d of the shaft 404. The shaft 404 can be configured to slidably mate with the frame 402 by passing through the opening 412. The shaft 404 can be configured to be slidably received in the opening 412 such that the shaft 404 can extend substantially parallel to the opening's longitudinal axis A11 and substantially parallel to the arm portion 402a of the frame 402.

The shaft 404 can include one or more openings 410a, 410b, 410c, 410d formed adjacent the distal end 404d of the shaft 404. When the shaft 404 and the frame 402 are mated together, the respective longitudinal axes A7, A8, A9, A10 of the holes 406a, 406b, 406c, 406d can be configured to pass through the one or more openings 410a, 410b, 410c, 410d formed in the shaft 404 and to intersect the inner lumen 408. Each one of the holes 406a, 406b, 406c, 406d can therefore be configured to predictably align with one of the openings 410a, 410b, 410c, 410d. A surgical device, e.g., a drill, a suture, etc., can thus be inserted through each of the holes 406a, 406b, 406c, 406d and predictably pass through the openings 410a, 410b, 410c, 410d and extend into the inner lumen 408 of the shaft 104. In an exemplary embodiment, each of the openings 410a, 410b, 410c, 410d can be configured to coaxially align with one of the holes 108a406a, 406b, 406c, 406d of the frame 402 when the frame 402 is mated to the shaft 404, as shown in FIG. 16.

The shaft 404 can include an alignment mechanism 414 configured to align the shaft 404 in a predetermined orientation relative to the frame 402 when the shaft 404 is received within the opening 412. The alignment mechanism 414 can therefore be configured to predictably coaxially align the each of the openings 410a, 410b, 410c, 410d with one of the holes 108a406a, 406b, 406c, 406d of the frame 402 when the frame 402 is mated to the shaft 404. The alignment mechanism 414 can have a variety of sizes, shapes, and configurations. Similar to the connector features and the surface features discussed above, the alignment mechanism can be in the form of visual marks, e.g., lines, colors, lights, symbols, etc., and/or tactile marks, e.g., grooves, etc., configured to align with corresponding surface feature(s) formed on the frame 402, e.g., on the base portion 402b adjacent the opening 412. The alignment mechanism can additionally or alternatively include a protrusion 414 configured to abut an exterior surface of the frame 402, e.g., an exterior surface of the base portion 402b as shown in FIG. 16. The frame 402 can include a corresponding surface feature (not shown) such as a depression configured to seat the alignment mechanism, and/or a line, symbol, or other mark configured to abut and/or align with the alignment mechanism, thereby helping to orient the shaft 404 in a proper longitudinal position and a proper rotational position relative to the frame 402 so as to optimally orient the openings 410a, 410b, 410c, 410d relative to the holes 406a, 406b, 406c, 406d.

Figure 18:
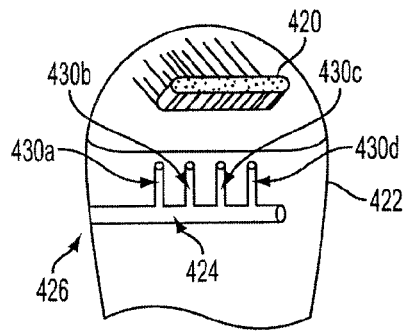
FIG. 18 is a side view of a tissue and of a bone having a tunnel formed therein and a plurality of transverse tunnels formed therein that intersect the tunnel.

Similar to the guide devices of FIGS. 1 and 3 discussed above, in use, the guide device 400 can facilitate formation of intersecting bone tunnels. As shown in FIG. 18, the guide device 400 can facilitate formation of a first bone tunnel 424 in a bone 422 of a patient and formation of a plurality of additional bone tunnels 430a, 430b, 430c, 430d in the bone 422. The additional bone tunnels 430a, 430b, 430c, 430d can be substantially parallel to one another and can each intersect the first bone tunnel 424, although similar to that discussed above, the additional bone tunnels 430a, 430b, 430c, 430d need not be substantially parallel to one another. More particularly, in an exemplary embodiment, the first bone tunnel 424 can be formed in the bone 422 similar to that discussed above regarding the first bone tunnel 124 of FIG. 8. The frame 402 can be positioned outside the patient relative to the bone 422 prior to forming the first bone tunnel 424. A surgical instrument, e.g., a drill (not shown), can then be advanced through the frame's opening 412 and into the bone 422 to form the first bone tunnel 424. By advancing the surgical instrument through the opening 412, the first bone tunnel 424 can be formed at a location in the bone 422 compatible with the size and shape of the guide device 400 and at a location relative to the bone 422 at which the additional bone tunnels 430*a*, 430*b*, 430*c*, 430*d* can be formed to optimally position a tissue 420 relative to the bone 422.

The additional bone tunnels 430*a*, 430*b*, 430*c*, 430*d* can be formed in the bone 422 similar to that discussed above regarding the additional bone tunnels 130*a*, 130*b*, 130*c* of FIG. 8, e.g., by drilling through each of the holes 406*a*, 406*b*, 406*c*, 406*d* formed in the frame 402. If the shaft 404 is not used to form the additional bone tunnels 430*a*, 430*b*, 430*c*, 430*d*, the shaft 404 can be advanced through the frame's opening 412 and be positioned within the first bone tunnel 424 prior to formation of the additional bone tunnels 430*a*, 430*b*, 430*c*, 430*d*. The presence of the first bone tunnel 424 in the bone 422 can indicate by feel when each of the additional bone tunnels 430*a*, 430*b*, 430*c*, 430*d* should stop being drilled, and/or an interior surface of the shaft 404 can help prevent the drill from drilling past the first bone tunnel 424.

Also similar to that mentioned above, after the additional bone tunnels 430*a*, 430*b*, 430*c*, 430*d* have been formed in the bone 422, the frame 402 can be rotated, e.g., about the longitudinal axis A11 of the opening 412 to position the frame 402 at a different position relative to the bone 422. The surgical instrument used to form the first bone tunnel 424, the shaft 404, or another surgical instrument can be inserted through the opening 412 and positioned within the first bone tunnel 424 to facilitate rotation of the frame 402 about the longitudinal axis A11 of the opening 412. One or more additional bone tunnels can be formed using the holes 406*a*, 406*b*, 406*c*, 406*d* as guides with the frame 402 in this secondary location relative to the bone 422.

Figure 19:
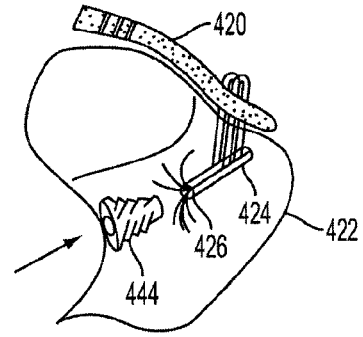
FIG. 19 is a perspective view of the tunnel and the transverse tunnels of FIG. 18 having a plurality of sutures extending therethrough and coupled to the tissue.

At least one suture can be positioned within the first bone tunnel 424 and at least one of the additional bone tunnels 430*a*, 430*b*, 430*c*, 430*d*. Similar to that discussed above regarding the at least one suture being positioned within the first bone tunnel 124 and at least one of the additional bone tunnels 130*a*, 130*b*, 130*c* of FIG. 8, the at least one suture can be positioned within the first bone tunnel 424 and at least one of the additional bone tunnels 430*a*, 430*b*, 430*c*, 430*d* in a variety of ways, such as by using the guide pin 132 of FIG. 10. In an exemplary embodiment, as shown in FIG. 19, first, second, and third sutures 434*a*, 434*b*, 434*c* can be positioned within the first bone tunnel 424 and various ones of the additional bone tunnels 430*a*, 430*b*, 430*c*, 430*d* for knotless repair. The first suture 434*a* can be positioned in the first, second, and third bone tunnels 424, 430*a*, 430*b*, the second suture 434*b* can be positioned in the first, third, and fourth bone tunnels 424, 430*b*, 430*c*, and the third suture 434*c* can be positioned in the first, fourth, and fifth bone tunnels 424, 430*c*, 430*d*. Ends of each of the first, second, and third sutures 434*a*, 434*b*, 434*c* can be pulled out of the first bone tunnel 324 through an anterior portal 426 such that their ends extend therefrom, similar to that discussed above. In an exemplary embodiment, the shaft 404 can be retracted through the opening 412 formed through the frame's base portion 402*a* with the suture 434*a*, 434*b*, 434*c* captured thereto, e.g., by extending through various ones of the openings 410*a*, 410*b*, 410*c*, 410*d* and into the shaft's inner lumen 408. Similar to that mentioned above, the 334*a*, 334*b*, 334*c* can be color-coded or otherwise uniquely identified.

Figure 20:
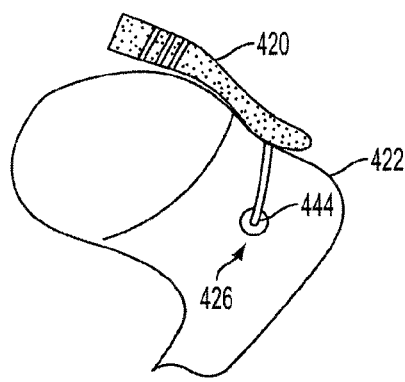
FIG. 20 is an anterior side view of the bone of FIG. 19 having the sutures secured therein.

The tissue 420 can be attached to each of the sutures 434*a*, 434*b*, 434*c*, and the sutures 434*a*, 434*b*, 434*c* can be tensioned to urge the tissue 420 into contact with the bone 422. The sutures 434*a*, 434*b*, 434*c* can be secured within the first bone tunnel 424 to secure the tissue 420 to the bone 422. The sutures 434*a*, 434*b*, 434*c* can be secured in a variety of ways, such as those discussed above regarding FIG. 14. As shown in FIGS. 19 and 20, a single fixation device, e.g., an interference screw 444, can be advanced into the first bone tunnel 424 through the anterior portal 426 and be secured in the first bone tunnel 424 by interference fit, threaded connection, cement, etc.

Figure 21:
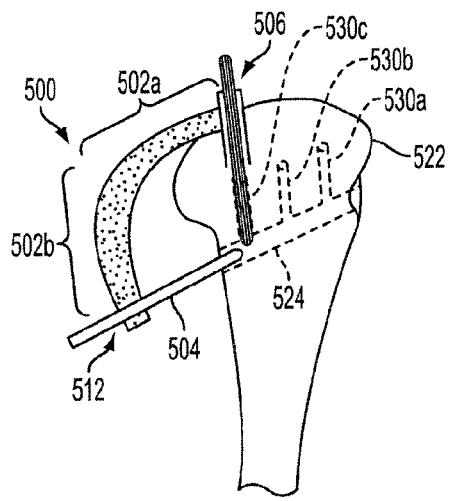
FIG. 21 is a perspective view of another embodiment of a guide device including an L-shaped frame, the frame being positioned adjacent a bone and having an elongate shaft advanced through an opening formed therethrough, the shaft being advanced into a tunnel formed in the bone.

FIG. 21 illustrates another embodiment of a frame 502 of a guide device 500. The device 500 can be configured and used similar to the guide device 400 of FIG. 15, but instead of including a plurality of holes formed in an arm portion 502*a* of the frame 502 similar to the frame 402 of FIGS. 15 and 16, the arm portion 502*a* of FIG. 21 includes a single hole 506 formed therethrough. The frame 502 can be configured to facilitate formation of a first bone tunnel 524 and can be configured to move relative to a bone 522 to sequentially form a plurality of bone tunnels 530*a*, 530*b*, 530*c* each using the hole 506 as a guide. Three bone tunnels 530*a*, 530*b*, 530*c* are formed in the illustrated embodiment, but any number of bone tunnels can be formed using the hole 506 as a guide. The bone tunnels 530*a*, 530*b*, 530*c* can be formed in any order.

A base portion 502*b* of the frame 502 can include an opening 512 formed therethrough that can be configured to slidably receive an elongate shaft 504 therein, similar to the opening 412 of FIG. 16 being configured to slidably receive the elongate shaft 404 of FIG. 16. The frame 502 can be configured to slide along the shaft 504 to be positioned in different positions relative to the bone 522 for formation of the plurality of bone tunnels 530*a*, 530*b*, 530*c* therethrough. The shaft 504 can have a plurality of surface features formed thereon, e.g., ruler marks, colored lines, etc., configured to facilitate positioning of the frame 502 therealong.

Figure 22:
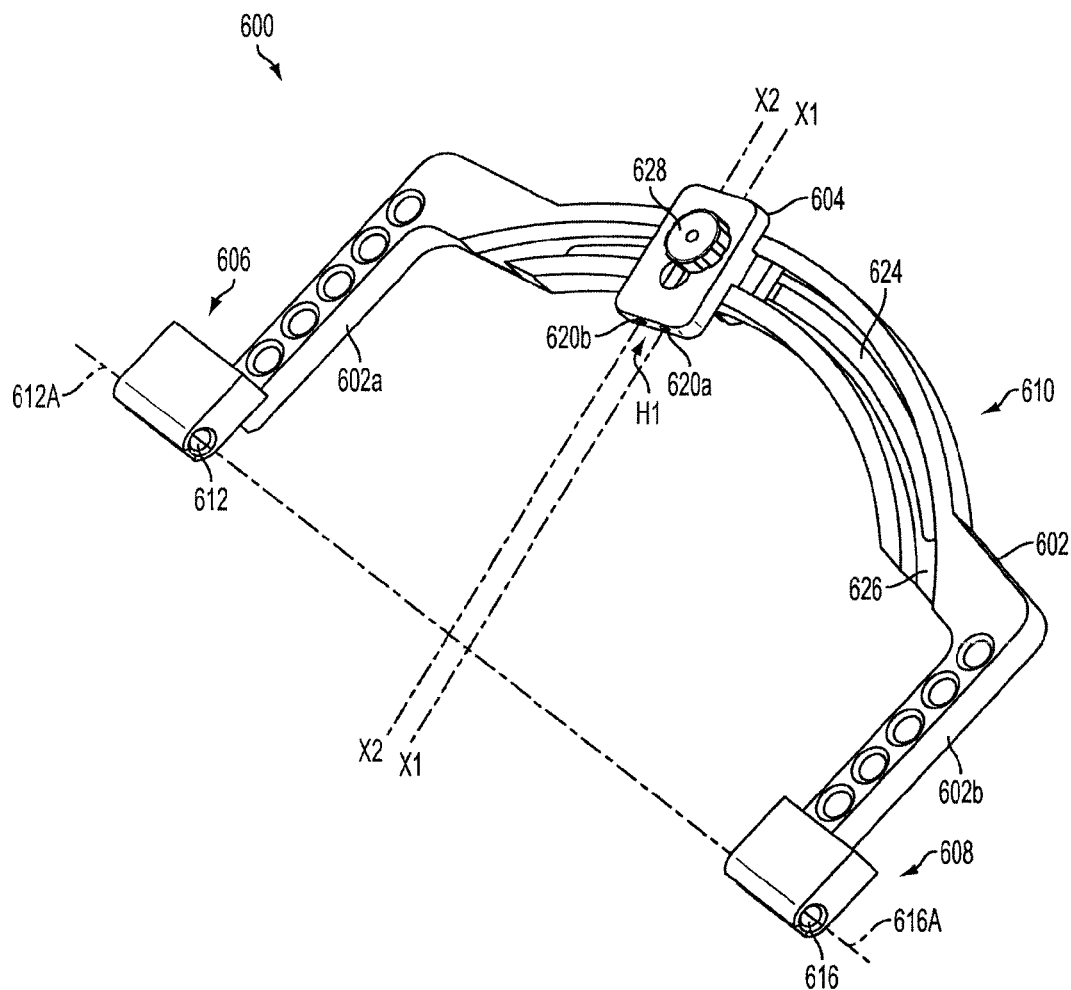
FIG. 22 is a perspective view of one embodiment of a guide device including a frame and a guide block mounted to the frame.
Figure 23:
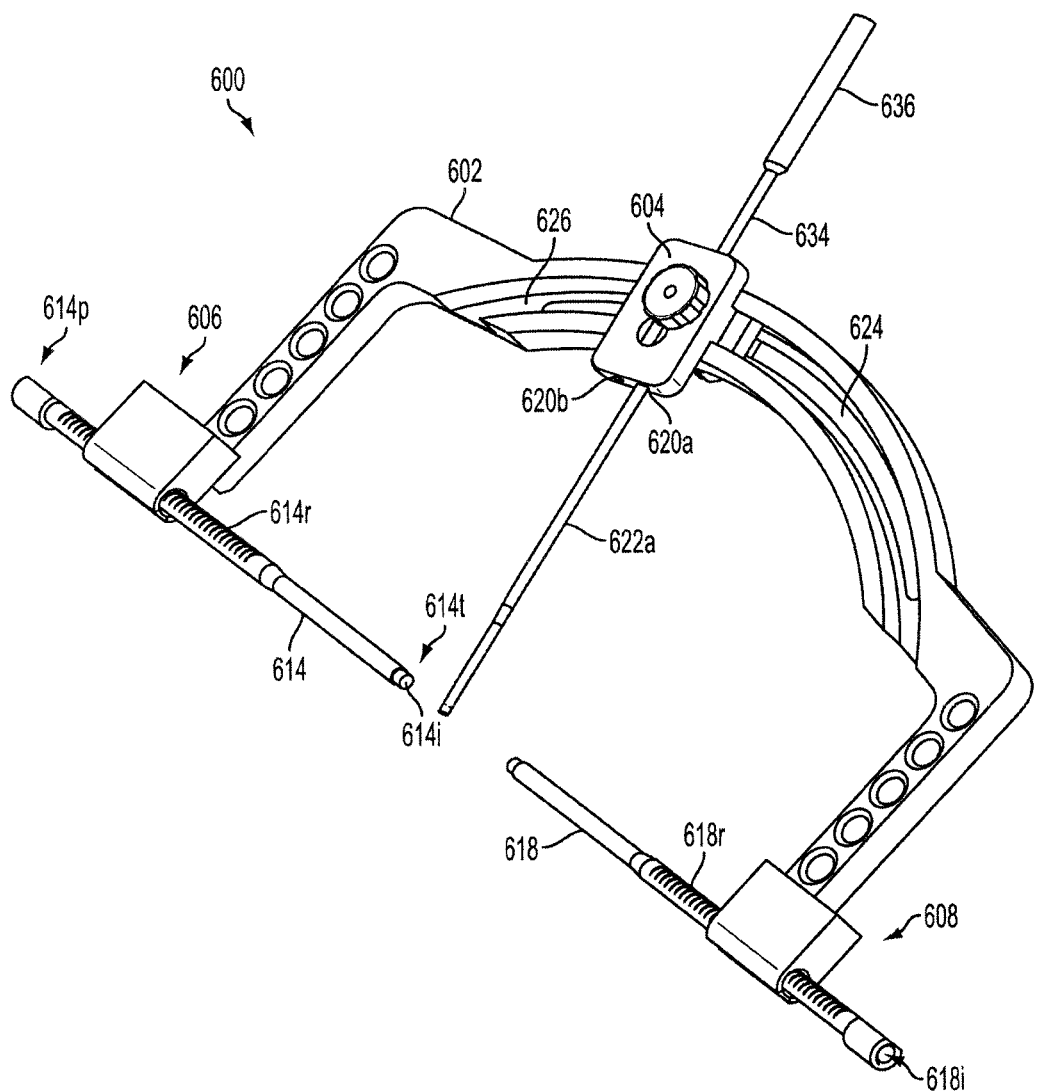
FIG. 23 is a perspective view of the guide device of FIG. 22 having a suture probe and two drill sleeves mated thereto.

FIGS. 22 and 23 illustrate another exemplary embodiment of a guide device 600 configured to aid in securing a tissue to bone by allowing multiple bone tunnels to be formed in the bone through which one or more sutures coupled to the tissue can be advanced to secure the tissue to the bone. The guide device 600 can include a frame 602 and a guide block 604 slidably coupled to the frame 602 such that the guide block 604 can be slidably movable along the frame 602 relative thereto. The guide block 604 can be configured to be locked at a selected position along the frame 602, such as with a thumbscrew 628, as discussed further below. The frame 602 can have a first end 606, a second end 608, and an arcuate portion 610 located between the first and second ends 606, 608. The arcuate portion 610 can extend linearly between first and second legs 602*a*, 602*b* of the frame 602 that can extend transversely from the arcuate portion 610. The first end 606 of the frame 602 can have a first bore 612 formed therethrough that can be configured to receive a first surgical instrument, e.g., a first cannulated drill sleeve 614, and the second end 608 of the frame 602 can have a second bore 616 formed therethrough that can be configured to receive a second surgical instrument, e.g., a second cannulated drill sleeve 618. A longitudinal axis 612A of the first bore 612 can be coaxial with a longitudinal axis 616A of the second bore 616. The guide block 604 can be slidably mounted on the arcuate portion 610 of the frame 602 and can have a third bore 620*a* that can be configured to receive a third surgical instrument, e.g., a first suture probe 622a, and a fourth bore 620b formed therethrough that can be configured to receive a fourth surgical instrument, e.g., a second suture probe (not shown).

Figure 24:
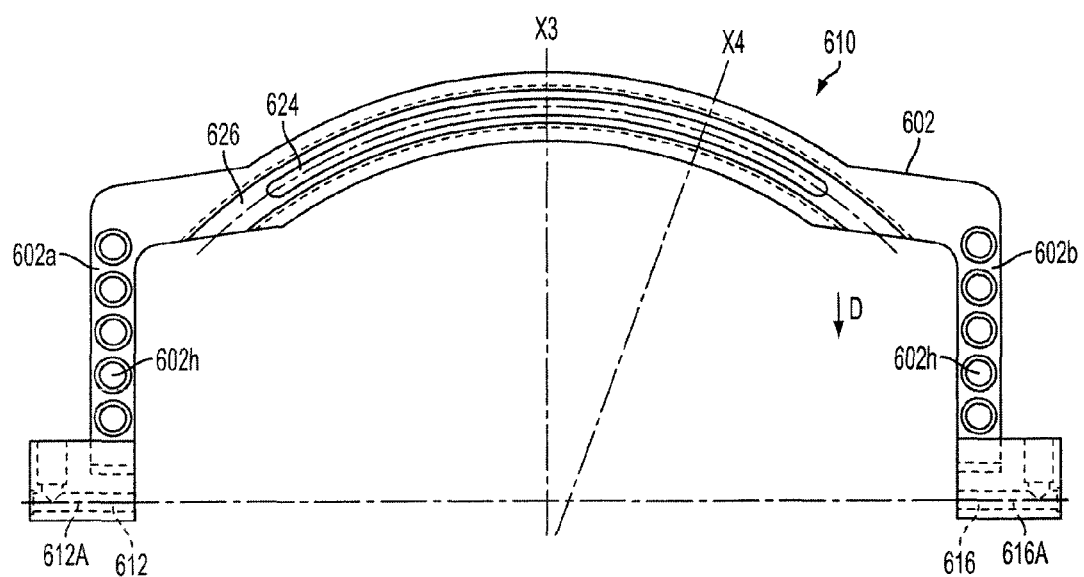
FIG. 24 is a side view of the frame of FIG. 22.
Figure 25:
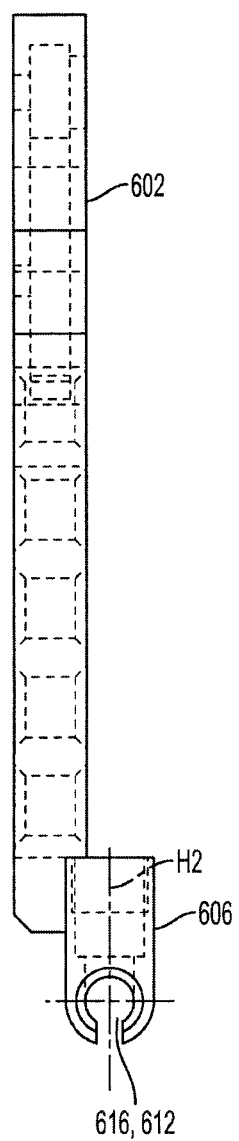
FIG. 25 is another side view of the frame of FIG. 22.

The frame 602 can have a variety of sizes, shapes, and configurations. FIGS. 24 and 25 illustrate the frame 602 without the guide block 604 mated thereto. As in the illustrated embodiment, the frame 602 can have a non-linear or non-straight shape, e.g., a u-shape. The non-linear or non-straight shape can facilitate positioning of the frame 602 entirely outside a patient's body by allowing the frame 602 to arc around the patient's body. Each of the legs 602a, 602b can be linear or straight as in this illustrated embodiment such that the guide member's u-shape can be a "hard" u-shape including two right angles. In another embodiment, the u-shape can be "soft." The arcuate portion 610 and each of the legs 602a, 602b can have any longitudinal length. Each of the legs 602a, 602b can have longitudinal lengths 602L equal to one another, which can facilitate formation of bone tunnels using the frame 602, as discussed further below.

The first and second legs 602a, 602b including the first and second ends 606, 608 at terminal ends thereof, respectively, can have a variety of sizes, shapes, and configurations. The legs 602a, 602b can be at least partially hollow and/or include one or more holes 602h formed therein as shown in the embodiment of FIGS. 22-24, or one or both of the legs 602a, 602b can be solid members. The holes 602h can be used to improve visibility of a surgical site, aid gripping of the frame 602, and/or help reduce a weight of the frame 602, which can help make the frame 602 easier to transport and to use during a surgical procedure. In addition to or as an alternative to the leg holes 602h, the arcuate portion 610 can include one or more holes formed therein.

A guide can be at each of the first and second ends 606, 608, and can each have at least one bore, e.g., the first and second bores 612, 616, formed therethrough. As in the illustrated embodiment, as shown in FIG. 25, the first and second bores 612, 616 can be spaced equidistantly from a horizontal center H2 of their respective guides, and can be offset vertically in their respective guides. The illustrated bores 612, 616 are cylindrical, but the bores 612, 616 can have any shape. As mentioned above, the longitudinal axes 612A, 616A of the first and second bores 612, 616, respectively, can be coaxial, which can allow bone tunnels to be formed using surgical instruments inserted through the bores 612, 616 can intersect one another and be coaxial.

In another embodiment, a frame can include ends with guides each having a plurality of bores formed therethrough. Each of the bores in one of the guides can have a corresponding coaxial bore in the other guide. The bores can be uniquely distinguishable from one another, e.g., color coded, marked or otherwise labeled, etc., to help indicate which of the bores in the two guides correspond to one another so instruments can be inserted through corresponding bores.

Figure 26:
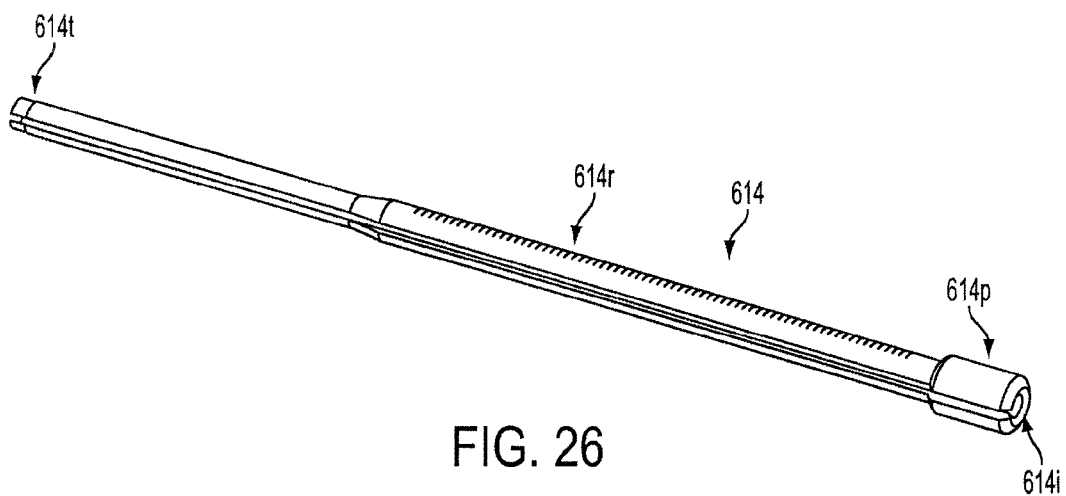
FIG. 26 is a perspective view of one of the drill sleeves of FIG. 23.
Figure 27:
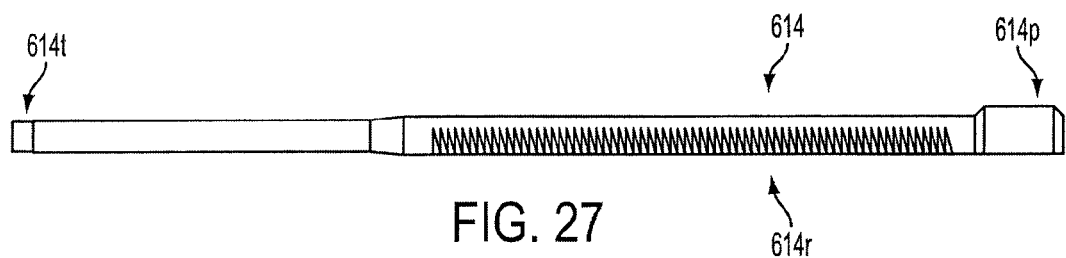
FIG. 27 is a side view of the drill sleeve of FIG. 26.
Figure 28:
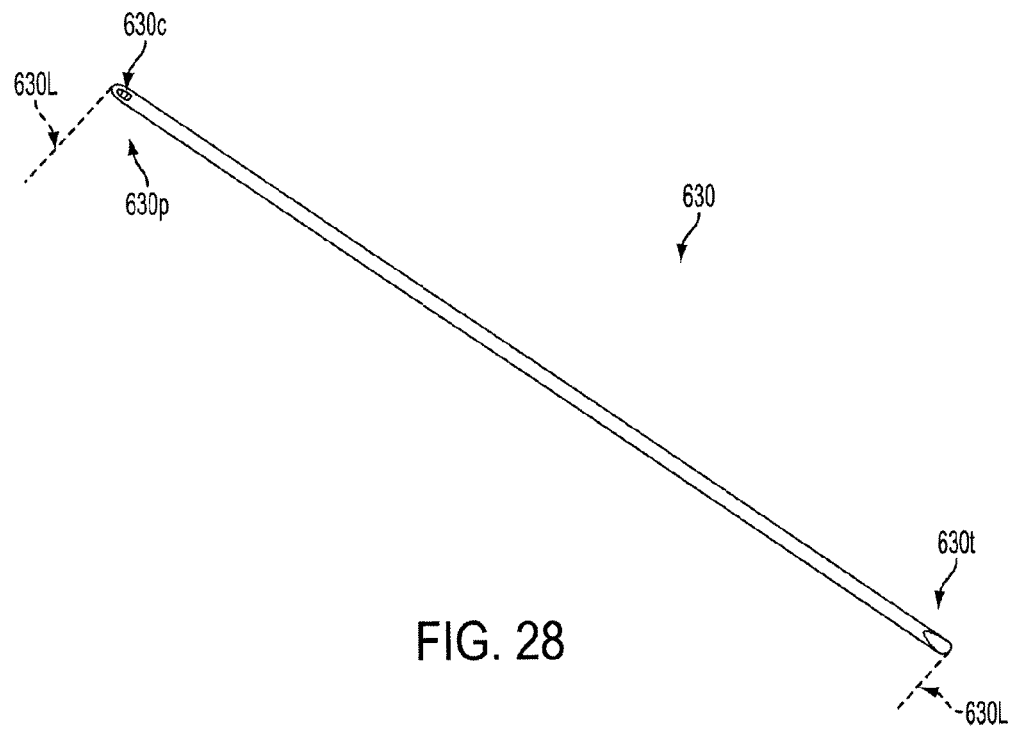
FIG. 28 is a perspective view of one embodiment of a drill.

As mentioned above, the first and second bores 612, 616 can be configured to receive instruments therethrough, such as drills and drill sleeves. As shown, for example, in FIG. 23, the first and second drill sleeves 614, 616 can be inserted through the first and second bores 612, 616, respectively, along the longitudinal axes 612A, 616A thereof. FIGS. 26 and 27 illustrate the first drill sleeve 614 as a standalone element representative of both drill sleeves 614, 618, which can be the same as one another. The drill sleeves 614, 618 can each be configured to receive a drill (not shown) therethrough such that a first drill extends through the first drill sleeve 614 and a second drill extends through the second drill sleeve 618. An exemplary embodiment of a drill 630 is illustrated in FIG. 28. Generally, the drill 630 can be a substantially rigid member and can be configured to form a bone tunnel in bone when inserted therein. As illustrated, the drill 630 can have a sharp distal tip 630t for penetrating and/or cutting bone. The drill 630 can have any longitudinal length 630L. In an exemplary embodiment, the drill's longitudinal length 630L can be about 18 inches.

The first and second drill sleeves 614, 618 can have a variety of configurations. As in the illustrated embodiment, the drill sleeves 614, 618 can each be substantially rigid members and can each include cannulated shafts configured to receive an instrument, e.g., a drill, through inner lumens 614i, 618i extending respectively therethrough. The drill sleeves 614, 618 and the drills can have any longitudinal lengths. In an exemplary embodiment, the drills have longitudinal lengths greater than their respective drill sleeves 614, 618 such that the drills can be received within their respective drill sleeves 614, 618 and have portions extending beyond both ends of the drill sleeves 614, 618. In other words, using the first drill sleeve 614 and the drill 630 as a non-limiting example, when the drill 630 is inserted through the sleeve 614, a distal cutting tip 630t of the drill 630 can be positioned distally beyond a distal tip 614t of the sleeve 614, and a proximal end 630p of the drill 630 can be positioned proximally beyond a proximal-most end 614p of the sleeve 614. The proximal end 630p of the drill 630 can include a connector feature 630c, which in the illustrated embodiment includes a crimp but can have other configurations, e.g., a magnet, an eyelet, etc. When inserted through the bores 612, 616, the drill sleeves 614, 618 can be configured to be axially and rotatably movable in their respective bores 612, 616.

As shown in FIGS. 23, 26, and 27, the first and second bullets, reamers, or drill sleeves 614, 618, generally referred to herein as "drill sleeves," can each include mating features configured to facilitate secure engagement of the drill sleeves 614, 618 with the frame 602. The frame 602, e.g., the guides at the first and second ends 606, 608 of the frame 602, can include corresponding mating features configured to engage the mating features of the drill sleeves 614, 618. Cooperation between the sleeves' and the frame's mating features can allow the drill sleeves 614, 618 to be held in a fixed, nonslidable position relative to the frame 602 when inserted through the first and second bores 612, 616, respectively. The mating features can have a variety of configurations, e.g., magnets, track/rail systems, threads, etc. In the illustrated embodiment, the drill sleeves 614, 618 each include mating features in the form of ratchets 614r, 618r along at least partial longitudinal lengths thereof. The ratchets 614r, 618r of the respective drill sleeves 614, 618 can be configured to engage corresponding teeth (not shown) formed within the bores 612, 616 to hold the drill sleeves 614, 618 in selected fixed positioned relative to the frame 602.

The distal ends of the sleeves 614, 618 can include one or more cutting teeth. flat tips, as shown in FIGS. 5-7. However, one or all of the drill sleeves 614, 618 can have other distal end configurations, such as flat, rounded, or conical tips. The cutting teeth can be configured to enhance cutting performance of the drill sleeve and to reduce an axial force needed for the cutting, such as when creating a bone tunnel. Various embodiments of drill sleeves and drills are further discussed in U.S. patent application Ser. No. 13/216,947 entitled "Cross Pinning Guide Devices and Methods" filed Aug. 24, 2011, which is hereby incorporated by reference in its entirety.

One or all of the drill sleeves 614, 618 can have a lubricated coating on its outer surface, inner surface, and/or on any other portions of the drill sleeves 614, 618. The lubricated coating can be formed on drill sleeves in any way, such as by fully dipping the drill sleeves in a validated Siliconization process. The lubricated coating can help facilitate smooth drilling bone holes, facilitate sleeve removal from bone, reduce heat generation during drilling, and/or reduce the potential for galling between bone and the sleeve, between the sleeve and a instrument inserted through and the sleeve, and between the sleeve and the guide. The coating can include any biocompatible lubricated coating, but in an exemplary embodiment, the coating can include Dow Corning® 630 Medical Fluid, available from Dow Corning Corporation of Midland, Mich.

In an exemplary embodiment, first and second drills can be inserted through the first and second drill sleeves 614, 618 and inserted through the first and second bores 612, 616 of the frame 602 to form converging, coaxial bone tunnels that result in a single bone tunnel. However, one or both of the first and second drills can be inserted directly through the first and second bores 612, 616, respectively, e.g., without drill sleeves. Additionally, although two drills can be inserted through the frame 602, in some embodiments, only one drill can be inserted through one of the frame's first and second bores 612, 616 to form a single bone tunnel.

The arcuate portion 610 can have a variety of configurations. The arcuate portion 610 can have an arcuate shape having an inner concave surface facing the guide rod legs 602a, 602b, such that the arcuate portion 610 can arc at a terminal end thereof in a direction D toward the first and second ends 606, 608 at ends of the first and second legs 602a, 602b, respectively, as shown in FIG. 24. The arcuate portion 610 can include a ruled scale (not shown), e.g., a plurality of angle degree marks, along at least a portion of its longitudinal length. The ruled scale can facilitate precise positioning of the guide block 604 along the arcuate portion 610, as discussed further below. The marks 126 can span any range and can have any increment, e.g., be in five degree increments from −25 degrees to 25 degrees. The arcuate portion 610 can include the ruled scale on opposed sides thereof, which can facilitate use of the frame 102 on both left and right sides of a patient's body, e.g., on left and right shoulders.

The arcuate portion 610 can have a groove 626 formed therein, which can facilitate smooth sliding of the guide block 604 along the arcuate portion 610. The groove 626 can be formed on one of the opposed sides of the arcuate portion 610, e.g., on one of the sides including a ruled scale, although any side(s) of the arcuate portion 610 can have a groove. In addition or in alternative to the groove 626, the arcuate portion 610 can include a longitudinal opening or slot 624 formed therein and extending through both opposed surfaces thereof. As in the illustrated embodiment, the slot 624 can be formed in a portion of the groove 626. The groove 626 and the slot 624 can be configured to facilitate sliding of the guide block 604 along the arcuate portion 610 and locking the guide block 604 relative thereto, as discussed further below.

First and second guide block axes X3, X4 shown in FIG. 24 illustrate sample axes of the third bore 620a formed through the guide block 604 when the guide block 604 is mated to the arcuate portion 610 of the frame 602 and first and second positions therealong. The first and second positions and the first and second guide block axes X3, X4 are non-limiting examples; the guide block 604 can be positioned anywhere along the arcuate portion 610 of the frame 602. As shown, the guide block axes X3, X4 can intersect the first and second bores' axes 612A, 612B regardless of the guide block's position along the arcuate portion 610 of the frame 602. The axis X2 of the fourth bore 620b can similarly intersect the first and second bores' axes 612A, 612B regardless of the guide block's position along the arcuate portion 610 of the frame 602.

The guide block 604 can have a variety of configurations. The guide block 604 can be configured to be detachably, slidably matable to the frame 602, or as in this illustrated embodiment, the guide block 604 can be configured to be non-removable, slidably mated to the frame 602, e.g., to the arcuate portion 610. The groove 626 and the slot 624 can be configured as guide paths for the guide block 604 along the arcuate portion 610 to facilitate smooth sliding thereof. The guide block 604 can be configured to selectively slide proximally and distally along the arcuate portion 610. As mentioned above, the guide block 604 can be locked at a particular position along the arcuate portion 610. The thumbscrew 628 can be configured to move between an unscrewed configuration, in which the guide block 604 can slide along the arcuate portion 610, and a screwed configuration, in which the guide block 604 is locked at the particular position along the arcuate portion 610 and cannot slide along the arcuate portion 610. In use, as discussed further below, when the guide block 604 is at a desired position along the arcuate portion 610, the thumbscrew 628 can be moved from the unscrewed configuration to the screwed configuration to lock the guide block's position. The thumbscrew 628 can move between the unscrewed and screwed configurations any number of times during a surgical procedure. Similarly, the guide block 604 can be slid any number of times and any distance along the arcuate portion 610.

The guide block 604 can have at least one bore formed therethrough that is configured to receive an instrument, e.g., a probe, a suture, a drill sleeve configured to receive a drill, etc. As mentioned above, the guide block 604 in the illustrated embodiment includes two bores 620a, 620b. A longitudinal axis X1 of the third bore 620a formed through the guide block 604 and a longitudinal axis X2 of the fourth bore 620b formed through the guide block 604 can be substantially parallel to one another, which can allow instruments inserted therethrough to be substantially parallel to one another. The bores' axes X1, X2 can each intersect the longitudinal axes 612A, 618A of the first and second bores 612, 618, as shown in FIG. 22, which can allow instruments inserted therethrough to intersect bone tunnels formed by instruments inserted through the first and second bores 612, 618, as discussed further below. Regardless of the location of the guide block 604 along the arcuate portion 610, the guide block 604 can be configured such that the bores' axes X1, X2 always intersect the longitudinal axes 612A, 618A of the first and second bores 612, 618, and hence any bone tunnels formed along the longitudinal axes 612A, 618A of the first and second bores 612, 618.

Each of the bores can be longitudinally formed through the guide block 604 such that when the guide block 604 is mated to the arcuate portion 610, the longitudinal axes X1, X2 of the third and fourth bores 620a, 620b can each be substantially parallel to the legs 602a, 602b, although similar to that discussed above, the longitudinal axes X1, X2 of the third and fourth bores 620a, 620b need not be substantially parallel to one another. As in the illustrated embodiment, the third and fourth bores 620a, 620b can be spaced equidistantly from a horizontal center H1 of the guide block 604. The third and fourth bores 620a, 620b can also be centered vertically in the guide block 604, as shown in FIG. 22. The illustrated third and fourth bores 620a, 620b are cylindrical, but the third and fourth bores 620a, 620b can have any shape.

Figure 29:
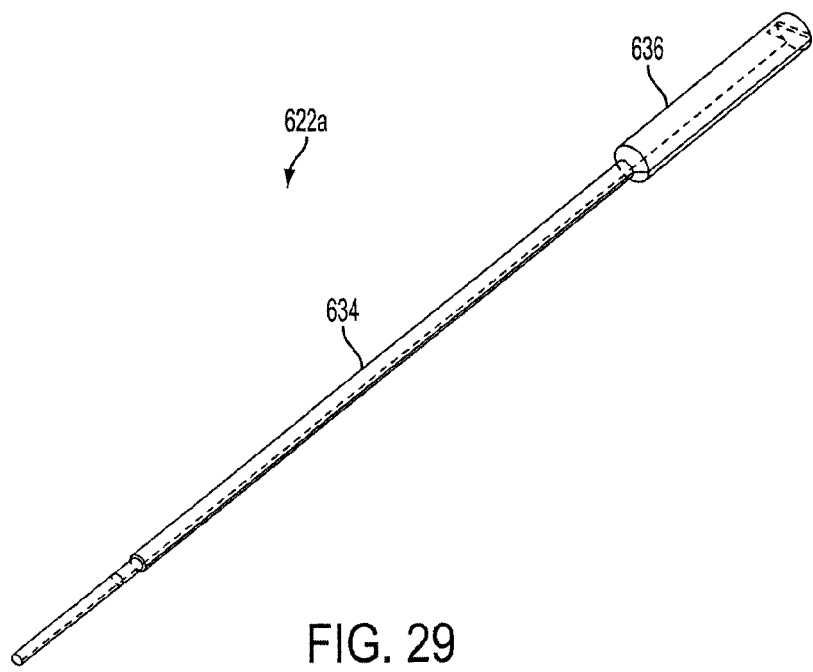
FIG. 29 is a perspective view of the suture probe of FIG. 23.
Figure 30:
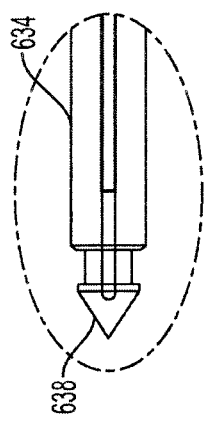
FIG. 30 is a side view of a distal tip of the suture probe of FIG. 29.

As mentioned above, each of the third and fourth bores 620a, 620b can be configured to have an instrument such as a suture probe advanced therethrough, e.g., the first suture probe 622a of FIGS. 23 and 29. The first suture probe 622a can have a variety of configurations. In an exemplary embodiment, the first suture probe 622a can be a substantially rigid member and include a cannulated elongate shaft 634 extending distally from a proximal collar 636. The elongate shaft 634 can have an outer diameter that is less than diameters of the third and fourth bores 620a, 620b, while the proximal collar 636 can have an outer diameter, at least at a distal end thereof, that is greater than the diameters of the third and fourth bores 620a, 620b. In this way, the proximal collar 636 can be configured as a stop to prevent the first suture probe 622a from being inserted too far into either of the third and fourth bores 620a, 620b and becoming difficult to handle. A distal tip 638 of the first suture probe 622a can be pointed, sharp, and/or otherwise configured to penetrate through tissue and/or bone. FIG. 30 shows the suture probe's distal tip 638 as having a pointed conical shape extending from a proximal cylindrical portion, although the distal tip can have other shapes. The distal tip 638 can be configured to be removable from the shaft 634, which can facilitate retrieval and tensioning of a suture coupled thereto, as discussed further below. The distal tip 638 can be removably coupled to the shaft 634 in a variety of ways, such as by having a proximal end thereof disposed within a distal end of the shaft 634 and mated thereto by interference fit.

Figure 31:
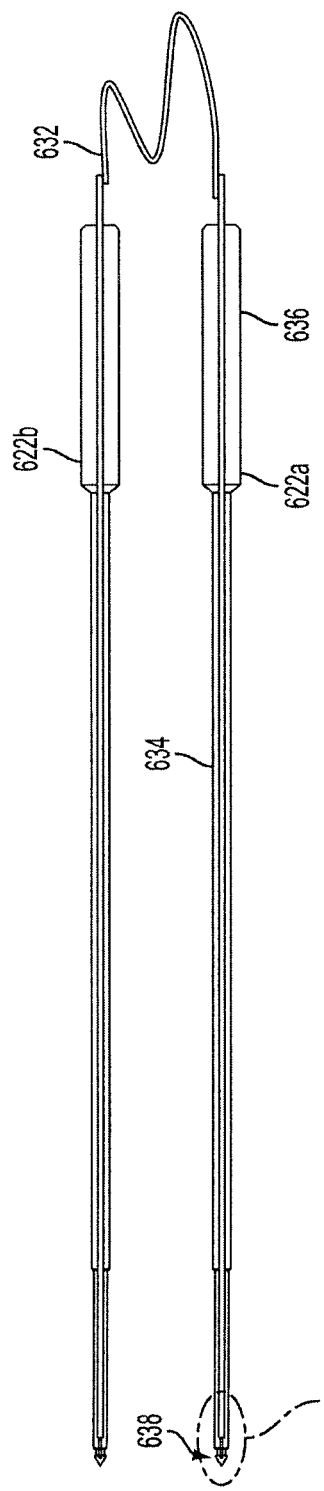
FIG. 31 is a side view of the suture probe of FIG. 29 coupled to a suture that is also coupled to another suture probe.

The first suture probe 622a is shown in FIGS. 23 and 29 as a standalone element without a suture coupled thereto. The first suture probe 622a can be advanced through one of the third and fourth bores 620a, 620b as such a standalone element without a suture coupled thereto, but in an exemplary embodiment, the first suture probe 622a can be coupled to a suture when advanced through one of the third and fourth bores 620a, 620b and can also be coupled to another suture probe, which can be advanced through the other of the third and fourth bores 620a, 620b. The suture probes advanced through the third and fourth bores 620a, 620b can vary from one another, but in the illustrated embodiment, the suture probes are the same as one another. FIG. 31 illustrates the first suture probe 622a coupled to a suture 632, the suture 632 also being coupled to a second suture probe 622b. The second suture probe 622b can be identical to the first suture probe 622a, as in the illustrated embodiment. The suture 632 coupled to the probes 622a, 622b is shown as a single, unfolded strand of suture, but the suture 632 can include multiple sutures and/or a folded suture. The first and second suture probes 622a, 622b can be provided pre-loaded with the suture 632, which can help ensure sterilization of the suture 632 and help save time during a surgical procedure.

Figure 32:
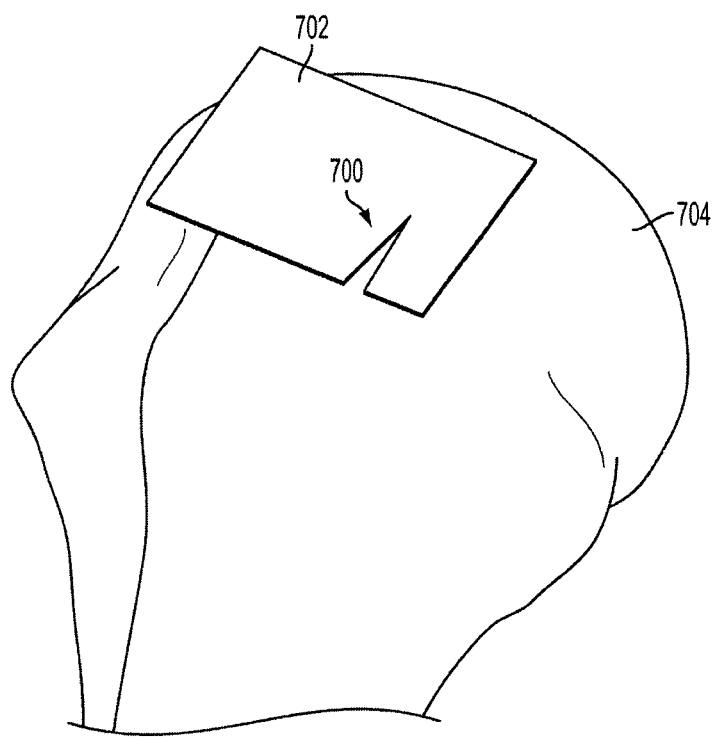
FIG. 32 is a perspective view of a bone adjacent a torn tissue.

The guide device 600 can be used a surgical procedure for tunnel repair. Although the rotator cuff repair procedure discussed below is illustrated with respect to the guide device 600 of FIG. 22 and various devices in FIGS. 23-31, any of the guide devices disclosed herein can be similarly used. Also, although the procedure is illustrated with respect to repairing a tear 700 in a rotator cuff tissue 702 at a shoulder bone 704 of a patient, as shown in FIG. 32, any of the guide devices disclosed herein can be used at a variety of anatomical locations to repair various tissue problems. Not shown in the Figures discussed below are skin incision(s) that can be used in performing various aspects of the procedure.

Generally, the patient can first be prepared for the surgery using standard techniques. In an exemplary embodiment illustrated in FIG. 33, the frame 602 can be positioned external to the patient relative to the bone 704 for formation of an anterior-posterior (AP) bone tunnel through the bone 704. The first end 606 of the frame 602 can be positioned on an anterior side of the bone 704, and the second end 608 of the frame 602 can be positioned on a posterior side of the bone 704. The arcuate portion 610 can be positioned above the tissue 702 to be repaired prior to the AP tunnel being formed, as shown in FIG. 3. However, the arcuate portion 610 can be at any position relative to the bone 704 and the tissue 702 prior to advancing one or more tools through the guide block 604 and into the patient because, as discussed further below, the AP tunnel can facilitate positioning of the arcuate portion 610 relative to the bone 704 and the tissue 702.

If the guide block 604 is configured to be detachable from the frame 602, the guide block 604 can be attached to the frame 602, e.g., to the arcuate portion 610, at any time during the procedure. In an exemplary embodiment, the guide block 604 can be mated to the arcuate portion 610 prior to the arcuate portion 610 of the frame 602 being positioned on the medial side of the bone 704 and/or prior to the AP tunnel being formed.

The AP tunnel can be prepared in a variety of ways, as will be appreciated by a person skilled in the art. For non-limiting example, the AP tunnel can be formed by determining a position in the bone 704 that has adequate depth and strength for having a suture passed therethrough for securing the tissue 702 to the bone 704. In an exemplary embodiment, the AP tunnel can be formed as close to the patient's superior cortex as possible. Although the AP tunnel can have one open end, e.g., be a blind tunnel, the AP tunnel can, as in this illustrated embodiment, have two open ends, which can allow both of the first and second drill sleeves 614, 618 to simultaneously be positioned within the bone 704 to help stabilize the frame 602 relative thereto, as discussed further below. In the illustrated embodiment, the AP tunnel is formed in an anterior to posterior direction, although the AP tunnel can be formed in a posterior to anterior direction.

Figure 33:
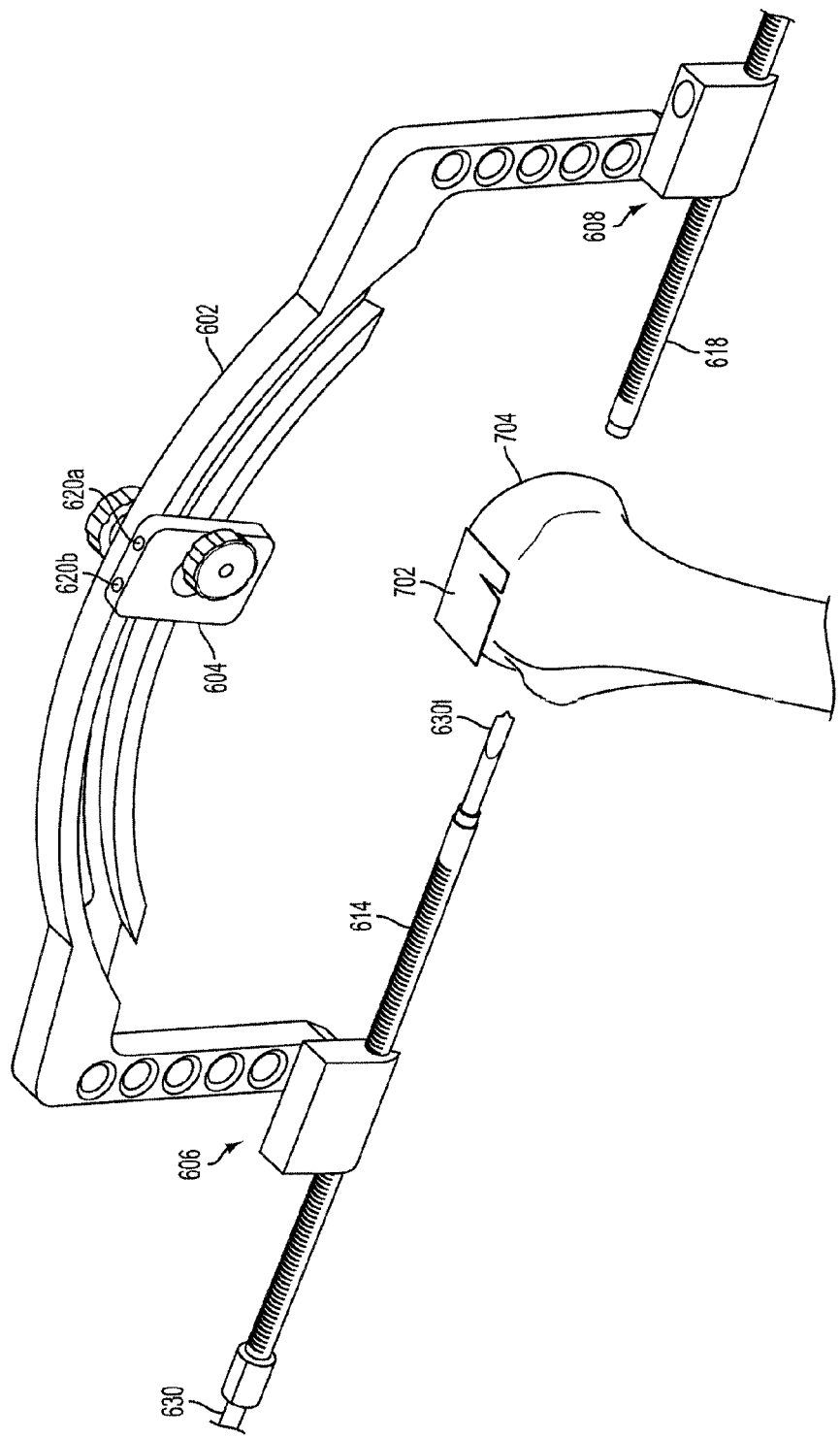
FIG. 33 is a perspective view of the guide device of FIG. 22 having the drill sleeves of FIG. 23 and the drill of FIG. 28 mated thereto, the guide device being positioned adjacent the bone and the tissue of FIG. 32.
Figure 34:
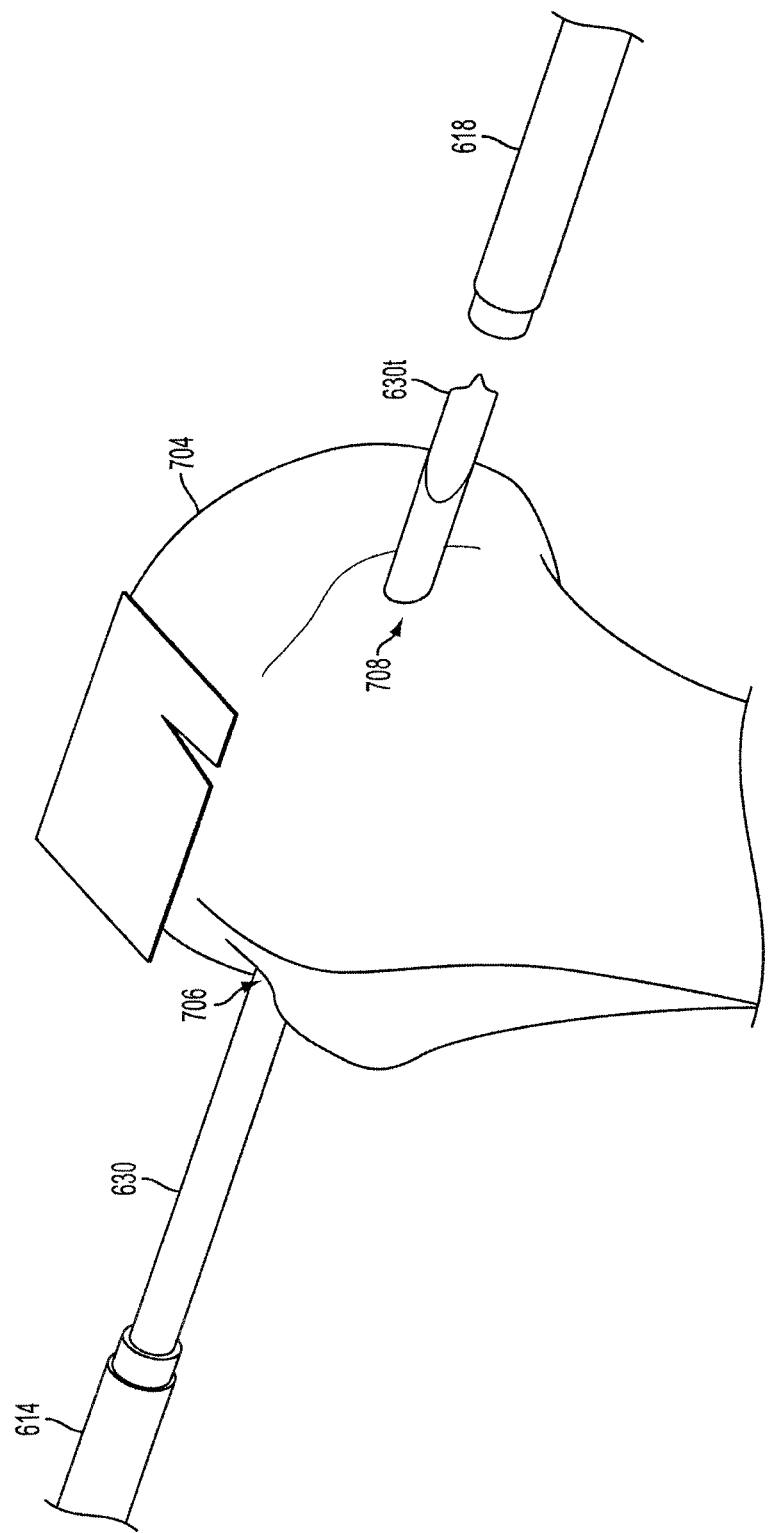
FIG. 34 is a perspective view of the drill of FIG. 33 advanced through the bone.

The first drill sleeve 614 and the drill 630 can be advanced through the first bore 612 formed in the first end 606 of the frame 602 positioned on the anterior side of the bone 704 in preparation of forming the AP tunnel. The second drill sleeve 618 can be advanced through the second bore 616 formed in the second end 608 of the frame 602 positioned on the posterior side of the bone 704, as shown in FIG. 33, which can facilitate assessment of a trajectory of the AP tunnel to be formed. The drill 630 can be advanced into the bone 704 by sliding through the first bore 612 and the first drill sleeve 614 to move along the first bore's longitudinal axis 612A. As shown in FIG. 34, the drill 630 can enter the bone 704 through an anterior portal 706 on the anterior side of the bone 704, pass through the bone 704, and exit the bone 704 through a posterior portal 708 on the posterior side of the bone 704. Because the first and second bores 612, 616 through which the sleeves 614, 618 are inserted are coaxial, the distal tip 630t of the drill 630 can pass out of the bone 704 and into the second drill sleeve 618, which can confirm an intended trajectory of the AP tunnel. One or both of the anterior and posterior portals 706, 708 can have a cannula (not shown) disposed therein prior to the drill 630 and/or the drill sleeves 614, 618 being advanced therethrough, which can help guide the drill 630 and/or the drill sleeves 614, 618 into the bone 704.

Figure 35:
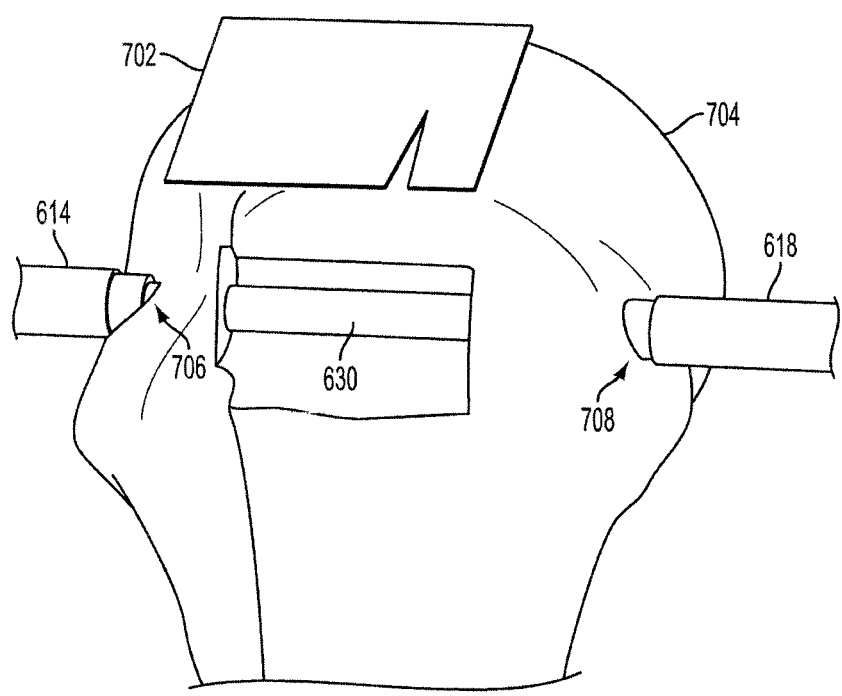
FIG. 35 is a perspective, partial cutaway view of the drill of FIG. 34 advanced through the bone and the drill sleeves of FIG. 33 advanced into the bone.

After formation of the AP tunnel, the sleeves 614, 618 can be advanced through their respective bores 612, 616 along their respective longitudinal axes 612A, 616A to have distal ends thereof be disposed within the bone 704, as shown in FIG. 35. The drill 630 can be disposed within the bone 704 and within the drill sleeves 614, 618 when the sleeves 614, 618 are advanced into the bone 704, as shown in FIG. 35, which can help guide the sleeves 614, 618 through the anterior and posterior portals 706, 708, respectively. The sleeves' ratchets 614r, 618r can fix the sleeves 614, 618 in position relative to the frame 602. Having one or both of the sleeves 614, 618 disposed within the bone 704 can therefore help stabilize the frame 602 relative thereto and can facilitate positioning of the arcuate portion 610 of the frame 602 relative to the bone 704. In one embodiment, with the sleeves 614, 618 inserted in the AP tunnel, the frame 602 can be rotated relative to the bone 704 about the longitudinal axes 612A, 616A of the first and second bores 612, 616, which can be coaxial with a longitudinal axis of the AP tunnel. Such rotation can facilitate positioning of the arcuate portion 610 above the tissue 702 on a medial side of the bone 704, as shown in FIG. 33.

Figure 36:
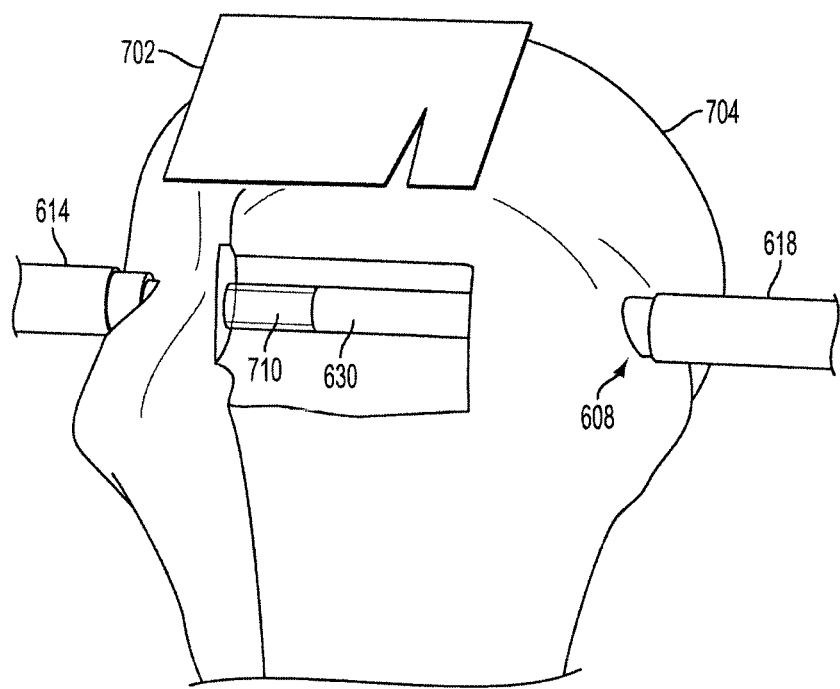
FIG. 36 is a perspective, partial cutaway view of the drill of FIG. 35 advancing a flexible tube into the bone.
Figure 37:
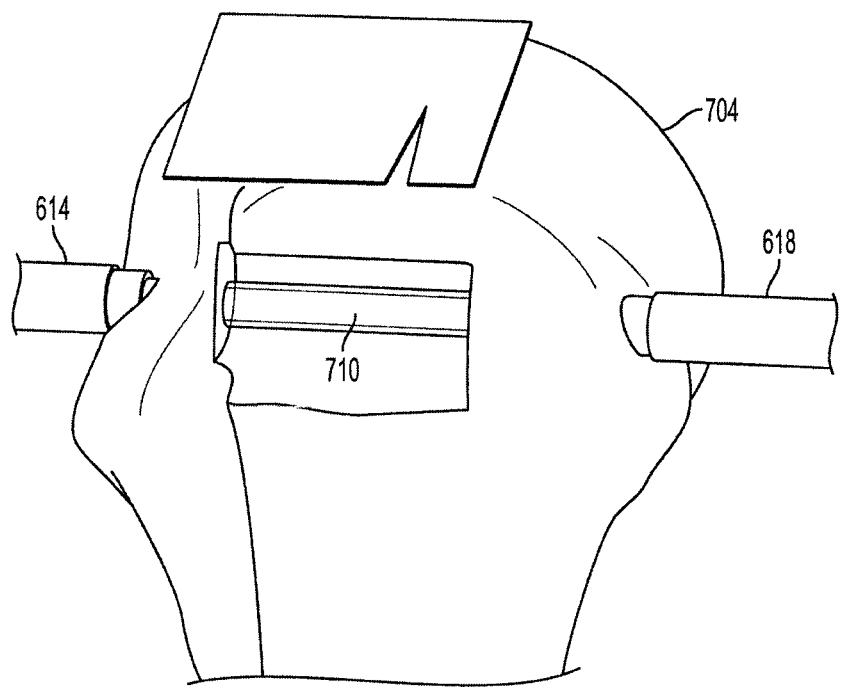
FIG. 37 is a perspective view of the flexible tube of FIG. 36 positioned within the bone.

A flexible tube 710, shown in FIG. 36 can be coupled to the proximal end 630p of the drill 630, such as by being crimped in the drill's crimp mating feature 630c. The flexible tube 710 can have a variety of sizes, shapes, and configurations. Generally, the flexible tube 710 can have a size and shape corresponding to a size and shape of the AP tunnel, e.g., substantially cylindrical as in the illustrated embodiment. The flexible tube 710 can be have a maximum outer diameter that is approximately the same as the diameter of the AP tunnel, which in the illustrated embodiment is about 4 mm. In an exemplary embodiment, the flexible tube 710 can include a plastic tube such as a Tygon® tube available from Saint-Gobain Performance Plastics of Aurora, Ohio. The drill 630 can be advanced in a posterior direction through the AP tunnel, as shown in FIG. 36, until the proximal end 630p of the drill 630 enters the AP tunnel, thereby introducing the flexible tube 710 into the AP tunnel. The drill 630 can continue being advanced through the AP tunnel until the drill 630 passes out of the AP tunnel, e.g., exiting through the posterior portal 708, such that the flexible tube 710 extends through the AP tunnel, as shown in FIG. 37. The flexible tube 710 can facilitate retrieval and tensioning of one or more sutures coupled to the tissue 702 and advanced into the AP tunnel, as discussed further below.

With the frame 602 having the guide block 604 mated thereto and being positioned on the medial side of the bone 704, the guide block 604 can be slid along the arcuate portion 610 of the frame 602 to position the guide block 604 at a selected angular position therealong to position the guide block 604 relative to the bone 704 and to the tissue 702, and/or the frame 604 can be rotated about the first bore's, second bore's and tunnel's coaxial axes 612A, 616A, to position the guide block 604 relative to the bone 704 and to the tissue 702. In this way, the trajectories of the third and fourth bores 620a, 620b in the guide block 604 can be angularly adjusted relative to the bone 704, to the tissue 702, and to the AP tunnel. The trajectories of the third and fourth bores 620a, 620b relative to the bone 704, to the tissue 702, and to the AP tunnel be selected based on any number of factors, such as where it is desired to pass a suture through one or both of the bores 620a, 620b and into the tissue 702 and the bone 704 with the guide block 604 at a particular selected position along the arcuate portion 610 of the frame 602. If the guide block 604 is in a locked configuration, e.g., if the thumbscrew 628 is in a screwed configuration, the thumbscrew 627 can be moved from the screwed configuration to an unscrewed configuration to allow the guide block 604 to slide along the arcuate portion 610 of the frame 602. When the guide block 108 is at a selected angular position, the guide block 604 can be locked at that position, such as by the moving the thumbscrew 628 from the unscrewed configuration to the screwed configuration.

Figure 38:
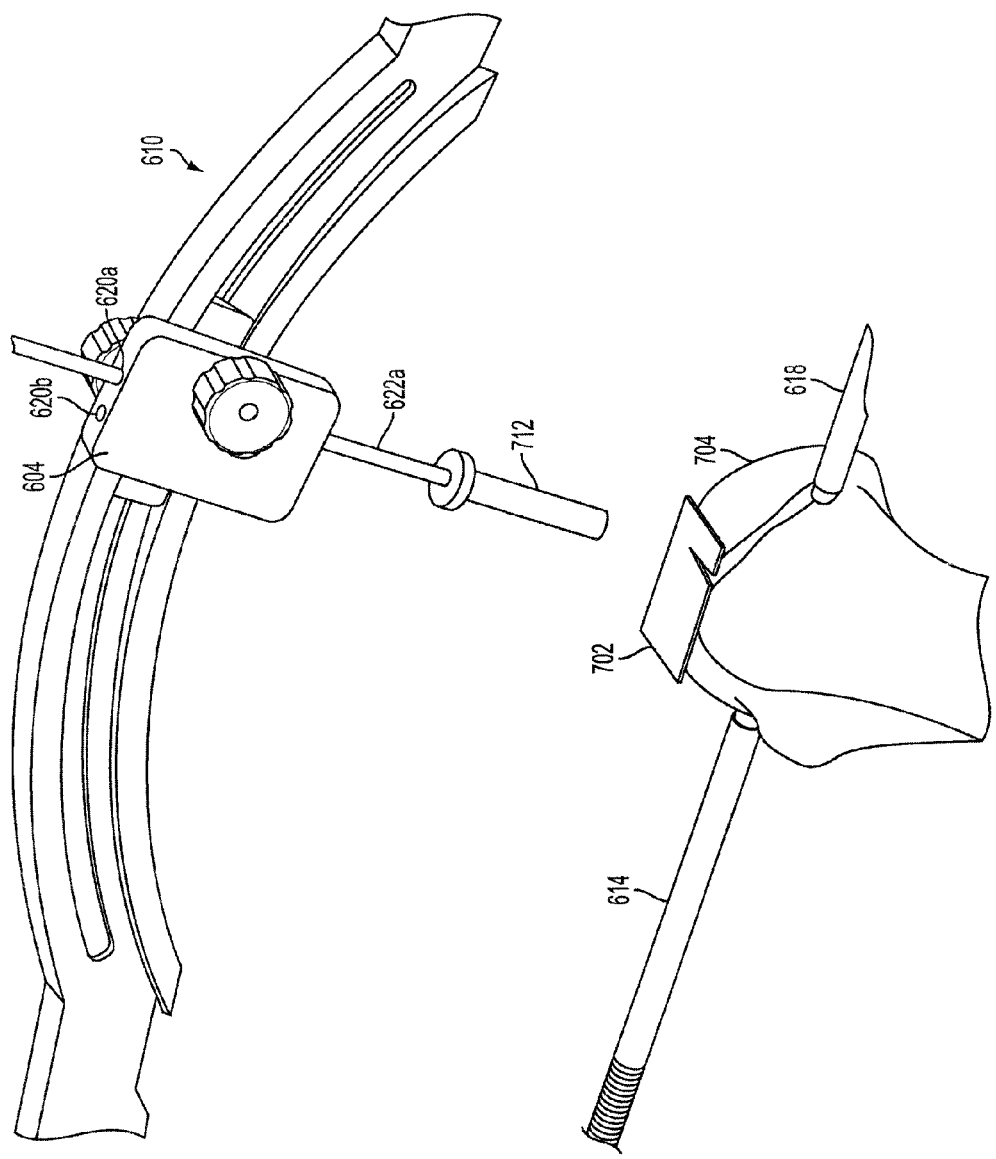
FIG. 38 is a perspective view of the suture probe of FIG. 23 with a suture coupled thereto advanced through the guide block coupled to the guide device of FIG. 33 and into a cannula toward the tissue and the bone of FIG. 37.
Figure 39:
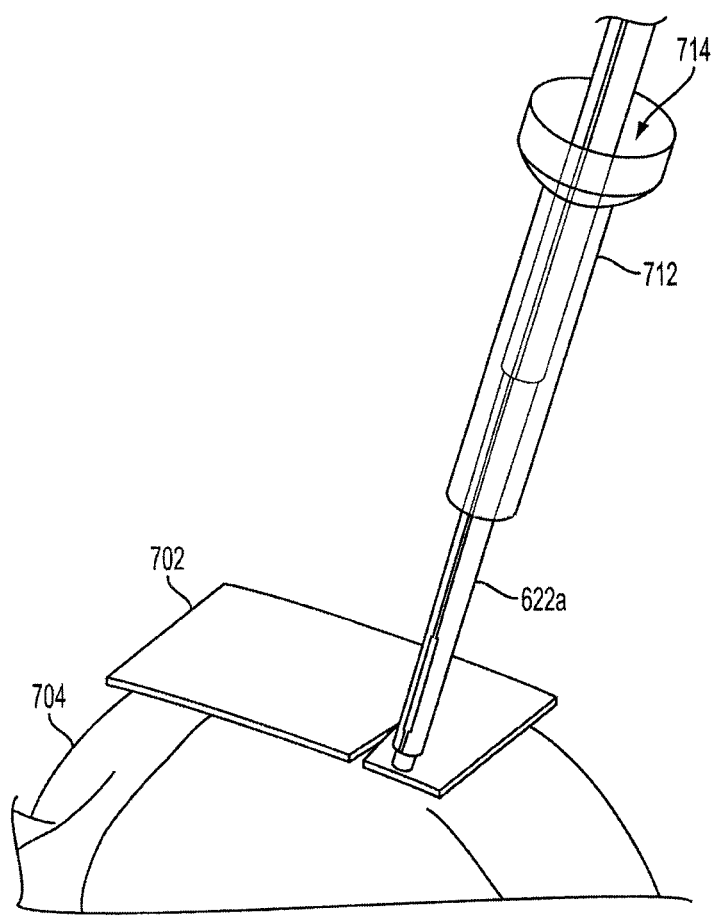
FIG. 39 is a perspective view of the suture probe of FIG. 38 advanced through the cannula and into the tissue.
Figure 40:
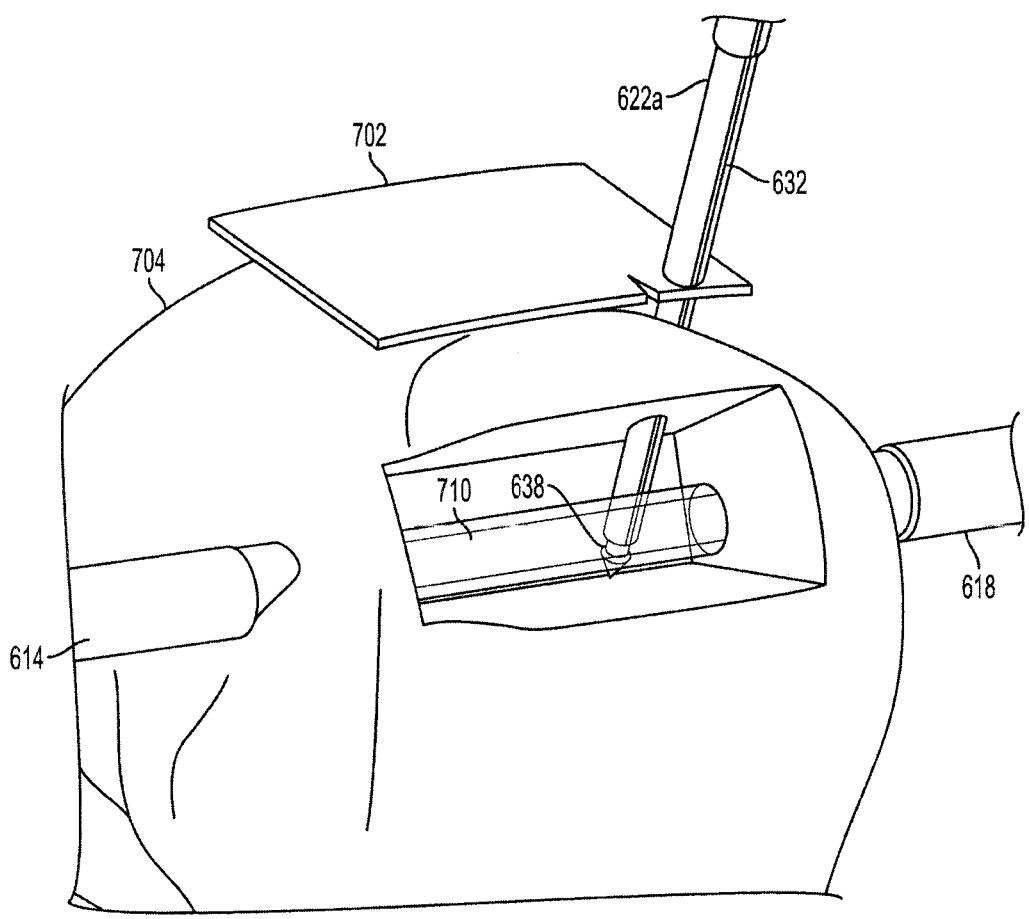
FIG. 40 is a perspective view of the suture probe of FIG. 39 advanced through the tissue and the flexible tube positioned in the bone.

With the guide block 604 at the selected angular position, as shown in FIG. 38, the first suture probe 622a having the suture 632 attached thereto can be advanced through the third bore 620a formed through the guide block 604. A cannula 712 can be positioned relative to the tissue 702 and the bone 704 to help guide the first suture probe 622a into the patient. The cannula 712 can be positioned entirely outside the bone 704 and either abut an external tissue surface, e.g., skin surface, of the patient, or pass through the external tissue surface a relatively small distance with a distal end of the cannula 712 being positioned above the tissue 702 to be secured to the bone 704. As shown in FIG. 39, the first suture probe 622a can be advanced through an interior passageway 714 of the cannula 712 to penetrate the tissue 702. The first suture probe 622a can be further advanced into the patient to pass through the tissue 702 and into the bone 704 underlying the tissue until the distal tip 638 thereof pierces the flexible tube 710 positioned within the AP tunnel and passes into the cannulated interior of the flexible tube 710, as shown in FIG. 40. The first suture probe 622a can be tapped into the bone 704, and the presence of the AP tunnel in the bone 704 can indicate by feel when each of the first suture probe 622a should stop being tapped into the bone 704. The first suture probe 622a can be configured to be inserted a predetermined depth into the bone 704 to position the distal tip 638 of the first suture probe 622a within the AP tunnel. The first suture probe 622a can include at least one stop feature configured to facilitate insertion of the first suture probe 622a into the bone 704 at the predetermined depth. The at least one stop feature can have a variety of configurations, such as a visual mark (e.g., a line, a color, a light, a symbol, etc.) configured to align with at least one corresponding stop feature of the guide block 604, a tactile mark (e.g., a groove, etc.) configured to align with at least one corresponding stop feature of the guide block 604, and/or a protrusion (e.g., a distal surface of the collar 636, a pin or other member extending radially outward from the shaft 634, etc.) configured to abut a surface of the guide block 604. The first suture probe 622a can be advanced through the guide block 604 until the at least one stop feature engages the at least one corresponding stop feature of the guide block 604, e.g., until the protrusion abuts the guide block and/or until stop features align, thereby indicating that the first suture probe 662a has been inserted into the bone 604 at the predetermined depth.

Figure 41:
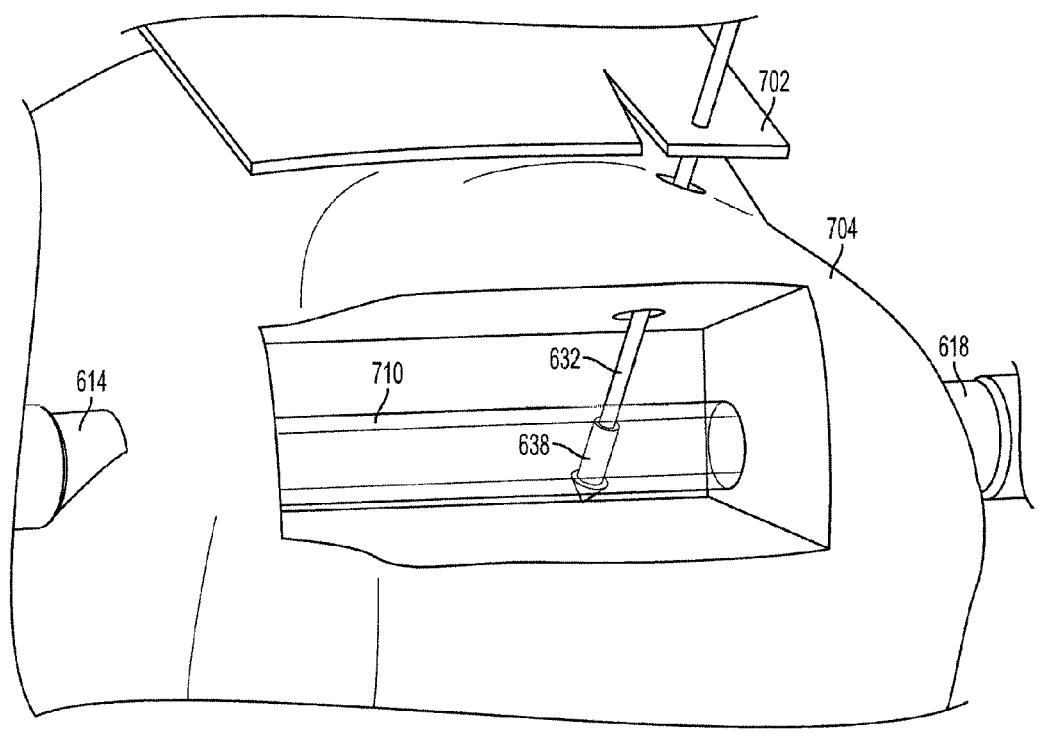
FIG. 41 is a perspective view of the suture of FIG. 40 advanced through the tissue and the flexible tube positioned in the bone.

As shown in FIG. 41, with the distal tip 638 of the first suture probe 622a positioned within the AP tunnel, the shaft 634 of the first suture probe 622a can be retracted to remove the shaft 634 from the patient's body, thereby leaving the distal tip 638 of the first suture probe 622a with the suture 632 attached thereto within the AP tunnel. The suture 632 can trail out of the AP tunnel, through the bone 704, through the tissue 702, and out of the patient.

Figure 42:
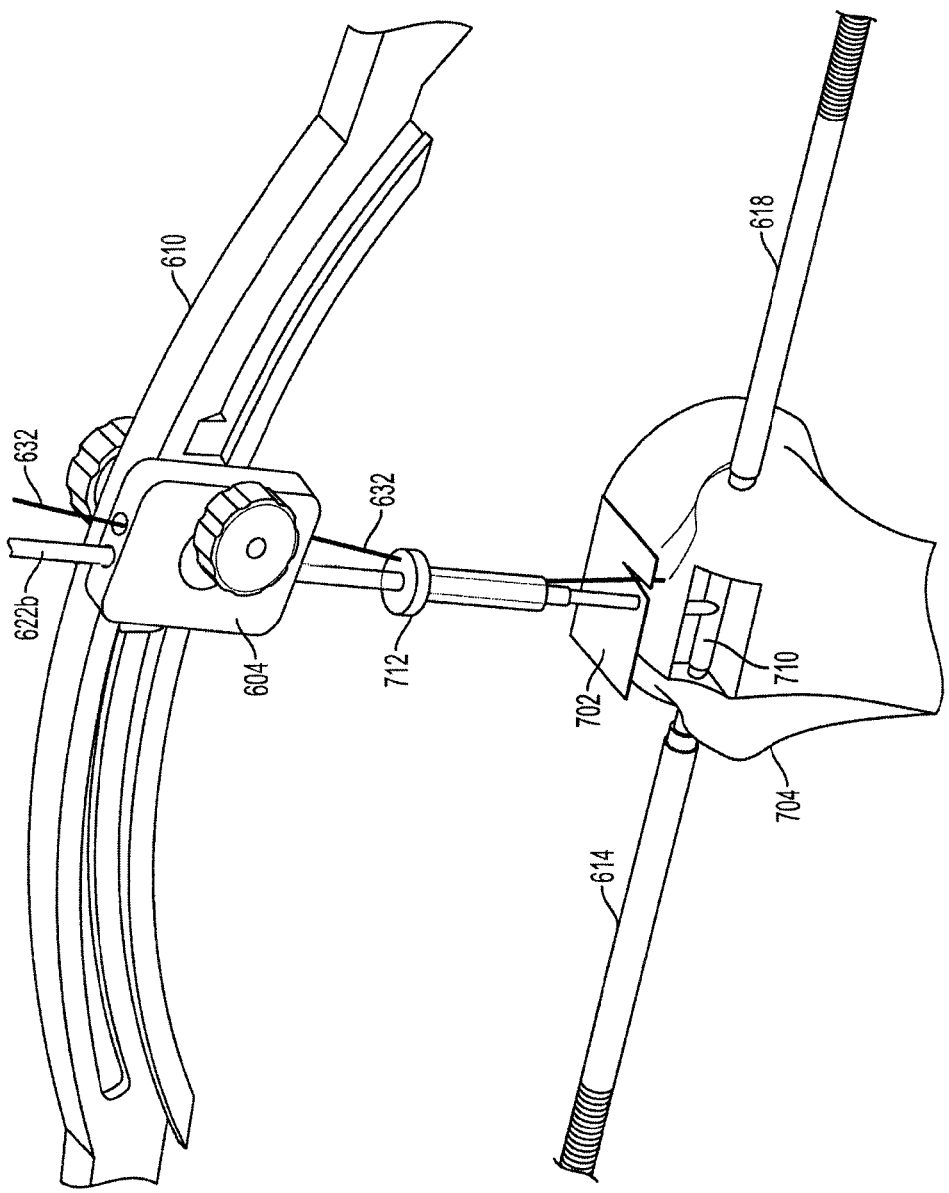
FIG. 42 is a perspective view of the other suture probe of FIG. 31 with the suture coupled thereto advanced through the guide block, the cannula, and the tissue and into the flexible tube of FIG. 41.

As shown in FIG. 42, the second suture probe 622b having the suture 632 coupled thereto can be advanced through the fourth bore 620b formed through the guide block 604 and be advanced into the patient similar to the first suture probe 622a. The second suture probe 622b can be advanced into the patient after the shaft 634 of the first suture probe 622a has been removed from the patient, as in the illustrated embodiment, or the second suture probe 622b can be advanced into the patient before removal of the shaft 634. Also, although the first and second suture probes 622a, 622b are advanced sequentially through the guide block 604 in the illustrated embodiment, the first and second suture probes 622a, 622b can be advanced simultaneously through the guide block 604. The guide block 604 can be at the same selected position along the arcuate portion 610 of the frame 602 when the first and second suture probes 622a, 622b are advanced through the guide block 604. Alternatively, the guide block 604 can be unlocked after the first suture probe 622a has been inserted into the patient, moved to a second selected position along the arcuate portion 610 of the frame 602, and locked at the second selected position. The second suture probe 622b can then be inserted through the fourth bore 620b with the guide block 604 at the second selected position. In the embodiment illustrated in FIG. 42, the guide block 604 has been so moved to the second selected position.

Figure 43:
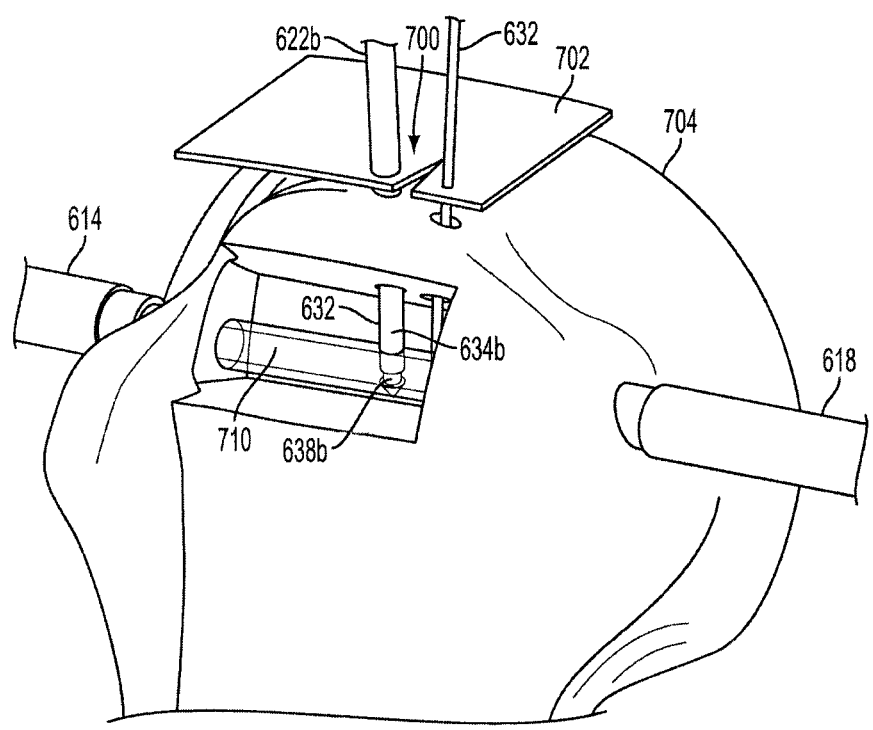
FIG. 43 is a perspective view of the other suture probe of FIG. 42 advanced through the tissue and the flexible tube positioned in the bone.
Figure 44:
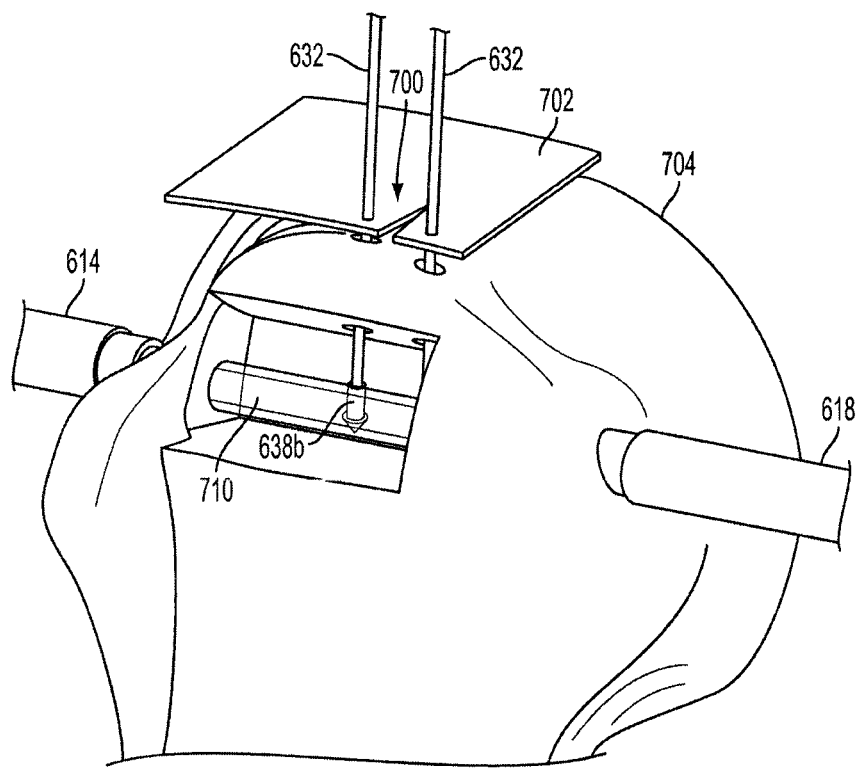
FIG. 44 is a perspective view of the suture of FIG. 43 advanced through the tissue and the flexible tube positioned in the bone.

Similar to that discussed above regarding the first suture probe 622a, the second suture probe 622b can be advanced into the patient to pass through the tissue 702 and into the bone 704 underlying the tissue until a distal tip 638b thereof pierces the flexible tube 710 positioned within the AP tunnel and passes into the cannulated interior of the flexible tube 710, as shown in FIG. 43. With the distal tip 638b of the second suture probe 622b positioned within the AP tunnel, a shaft 634b of the second suture probe 622b can be retracted to remove the shaft 634b from the patient's body, thereby leaving the distal tip 638b of the second suture probe 622b with the suture 632 attached thereto within the AP tunnel. Thus, as shown in FIG. 44, the suture 632 can have first and second portions 632a, 632b trailing out of the AP tunnel, through the bone 704, through the tissue 702, and out of the patient, with each of the portions 632a, 632b having one of the probe distal tips 638, 638b coupled thereto (the first distal tip 638 is obscured in FIG. 44). An intermediate portion 632i of the suture 632i can be positioned outside the AP tunnel and above the tissue 702. The position of the fourth bore 620b formed through the guide block 604 can allow the second suture probe 622b, and hence the suture 632, to be advanced through the tissue 702 on an opposite side of the tear 700 from the first suture probe 622a, as shown in FIGS. 43 and 44.

Figure 45:
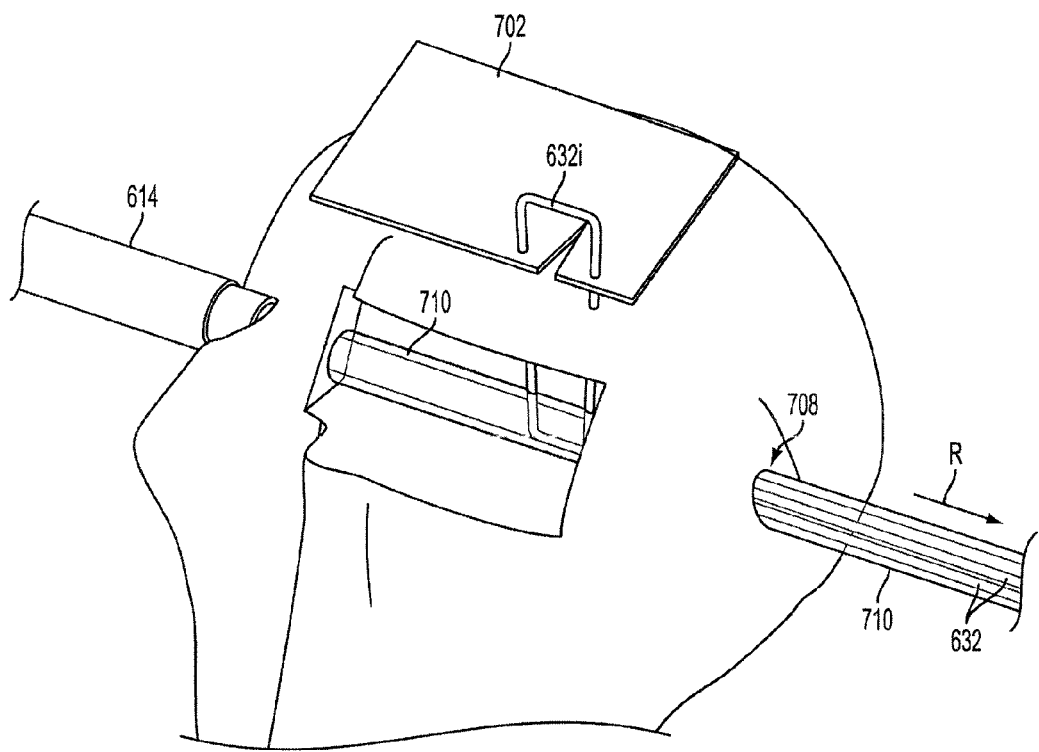
FIG. 45 is a perspective view of the flexible tube of FIG. 44 being removed from the bone and advancing the suture therewith.
Figure 46:
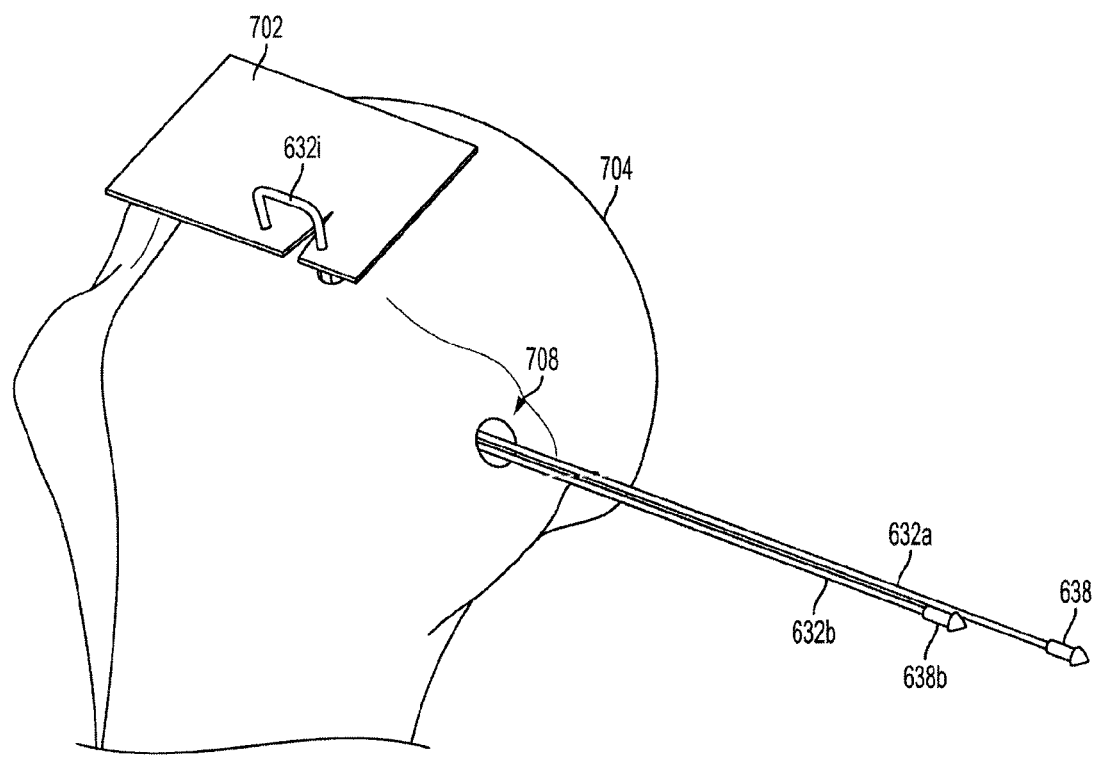
FIG. 46 is a perspective view of the suture of FIG. 45 advanced out a posterior portal of the bone.
Figure 47:
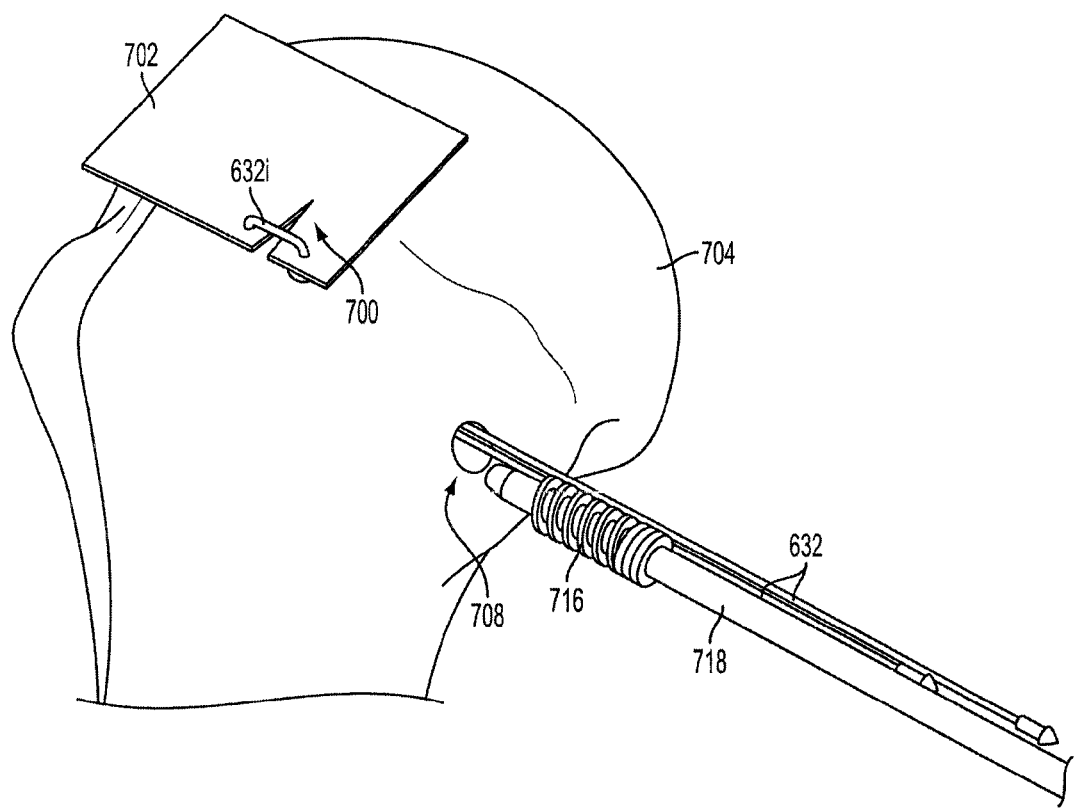
FIG. 47 is a perspective view of the suture of FIG. 46 tensioned and of a fixation device advancing toward the posterior portal.
Figure 48:
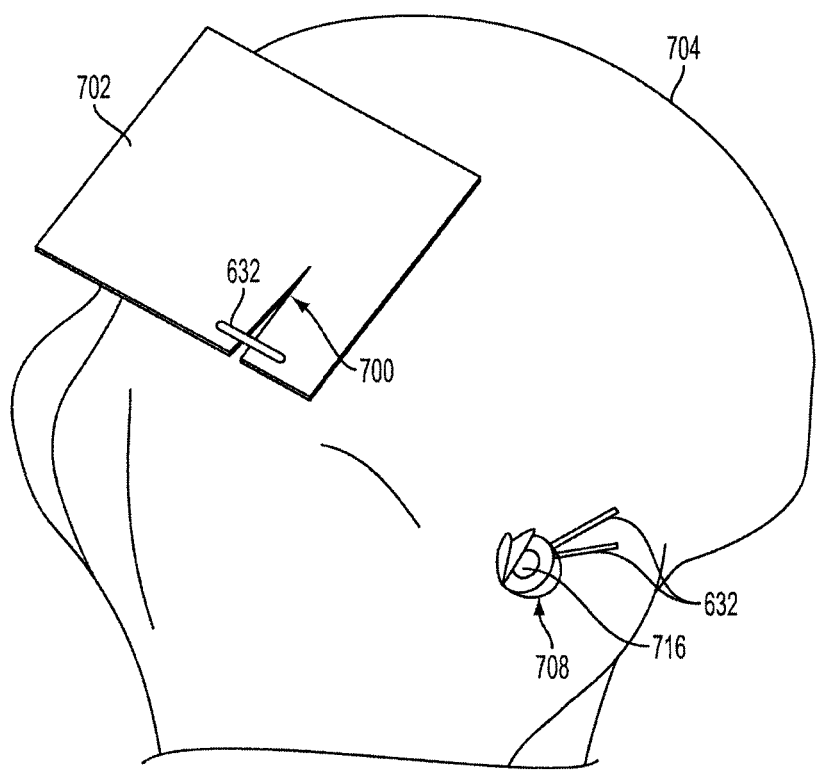
FIG. 48 is a perspective view of the fixation device of FIG. 47 advanced into the posterior portal and securing the suture therein.

The flexible tube 710 can be moved in a posterior direction, as indicated by arrow R in FIG. 45, through the posterior portal 708. For clarity, the second drill sleeve 618 is not shown in FIG. 45. The movement of the flexible tube 710 can also move the probe distal tips 638, 638b in the posterior direction and hence also move posteriorly the first and second portions 632a, 632b of the suture 632 coupled to the probe distal tips 638, 638b. The posterior movement of the first and second portions 632a, 632b of the suture 632 can cause the intermediate portion 632i of the suture 632 to advance toward the tissue 702, as also shown in FIG. 45. The intermediate portion 632i of the suture 632 can span across the tear 700, which can facilitate closure and healing of the tear 700. Once the probe distal tips 638, 638b having the first and second portions 632a, 632b of the suture 632 coupled thereto have been pulled a sufficient amount to be located external to the patient, as shown in FIG. 46, the flexible tube 710 can be removed from the suture 632, and the drill sleeves 614, 618 can be removed from the bone 704. If the cannula 712 has been inserted into the patient, the cannula 712 can be removed therefrom. The suture 632 can be tensioned, e.g., the first and second portions 632a, 632b of the suture 632 can be pulled, to move the intermediate portion 632i of the suture 632 closer to the tear 700, as shown in FIG. 47. The intermediate portion 632i of the suture 632 can abut the tissue 702 while spanning the tear 700.

After tensioning the suture 632 to position the suture 632 and the tissue 702 coupled thereto in a desired position relative to the bone 704, and after tensioning and position any additional sutures, a single fixation device 716 can be advanced into the posterior portal 708 of the AP tunnel through which the suture 632 extends to secure the sutures 432, as shown in FIGS. 45 and 46. Excess suture 632 can be trimmed.

The fixation device 716 can be advanced into the posterior portal 708 in a variety of ways, as will be appreciated by a person skilled in the art. In an exemplary embodiment, as shown in FIG. 45, the fixation device 716 can be coupled to a distal end of a driver 718 and advanced into the posterior portal 708. The driver 718 can then be removed from the fixation device 716 and removed from the patient. Although the fixation device is illustrated as a suture anchor in FIG. 14, the fixation device can have a variety of configurations, e.g., a screw, a suture anchor, cement, a pin, etc. The suture anchor can also have a variety of configurations. Exemplary embodiments of suture anchors include the HEALIX BR™ anchor and the HEALIX PEEK™ anchor, both available from DePuy Mitek, Inc. of Raynham, Mass.

One or more additional sutures (not shown) can be advanced into the patient similarly to the suture 632 to help further secure the tissue 702 to the bone 704 and repair the tear 700. Each of the one or more additional sutures can be advanced into the tissue 702 and into the bone 704 at a different location from the suture 632 and from each other. The guide block 604 can be slid along the arcuate portion 610 of the frame 602 to redirect the trajectories of the third and fourth bores 620a, 620b for each of the one or more additional sutures and/or the frame 602 can be rotated relative to the tissue 702 and the bone 704 about the AP tunnel's longitudinal axis, e.g., the first and second bores' axes 612A, 616A, to redirect the trajectories of the third and fourth bores 620a, 620b for each of the one or more additional sutures. Providing multiple sutures in different locations can provide redundancy in case of suture failure and can help urge the tissue 702 into greater contact with the bone 704, which can facilitate healing and can help keep the tissue 702 in greater contact with the bone 704 as the patient moves. The suture 632 and each of the one or more additional sutures can be color-coded or otherwise marked for unique identification. The flexible tube 710 can be used to advance each of the one or more additional sutures through the posterior portal 708. The single fixation device 716 can be used to secure the suture 632 and each of the one or more additional sutures.

The various methods and devices disclosed herein can be used in a variety of surgical procedures, however the methods and devices are particularly useful for repairing a torn rotator cuff in a human shoulder.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising: a frame having a base portion and an arm portion extending transversely from the base portion, the base portion having an opening formed therethrough, and the arm portion having a plurality of holes formed therethrough, the opening formed through the base portion being configured to receive a surgical instrument therethrough, each of the plurality of holes being configured to receive a suture therethrough, a longitudinal axis of the opening formed through the base portion being substantially perpendicular to longitudinal axes of each of the plurality of holes, and the longitudinal axes of the plurality of holes being substantially parallel to one another; a shaft having a cannulated interior and being configured to be slidably seated in the opening, wherein when the shaft is slidably seated in the opening, the longitudinal axis of each of the plurality of holes intersects the cannulated interior of the shaft; a first suture configured to, when the shaft is slidably seated in the opening, extend through a first one of the plurality of holes, into the cannulated interior of the shaft, and through the opening formed through the base portion of the frame; and a second suture configured to, when the shaft is slidably seated in the opening, extend through a second one of the plurality of holes, into the cannulated interior of the shaft, and through the opening formed through the base portion of the frame.

2. The device of claim 1, further comprising a suture capture device having at least one suture capture feature, the suture capture device being configured to be advanced through the opening such that at least one suture capture feature is aligned with at least one of the holes.

3. The device of claim 1, further comprising a suture capture device configured to be advanced through the opening formed through the base portion to capture at least one suture extending through at least one of the plurality of holes, and retracted through the opening formed through the base portion with the at least one suture captured thereto.

4. The device of claim 1, wherein the shaft is configured to be inserted into bone.

5. The device of claim 4, wherein when the shaft is slidably seated in the opening and the shaft is positioned within the bone, an intermediate portion of the shaft extending between a first end of the shaft and a second end of the shaft is positioned within the bone and is positioned relative to the arm portion of the frame such that respective longitudinal axes of the plurality of holes intersect a longitudinal axis of the intermediate portion of the shaft.

6. The device of claim 5, wherein the shaft has a plurality of openings formed in the intermediate portion thereof, and, when the shaft is slidably seated in the opening, each of the plurality of openings is coaxially aligned with one of the plurality of holes.

7. The device of claim 1, wherein the shaft includes an alignment feature configured to align the shaft in a predetermined orientation relative to the holes.

8. The device of claim 7, wherein the frame include a surface feature configured to align with the alignment feature when the shaft is slidably seated in the opening so as to align the shaft in the predetermined orientation relative to the holes.

9. The device of claim 1, wherein the cannulated interior is configured to receive therein the suture that is received by each of the plurality of holes.

10. A surgical device, comprising: a guide device having first and second terminal ends with an intermediate portion extending between the first and second terminal ends, a first plurality of holes being formed in the intermediate portion, and the first terminal end including an opening therein; a shaft having one or more holes formed therein, the shaft having an inner lumen extending therethrough that is in communication with the one or more holes, the shaft being configured to be releasably received in the opening such that longitudinal axes of each of the first plurality of holes pass through the one or more holes, and the shaft being configured to be advanced into a bone of a patient; wherein when the shaft is positioned within the bone and is releasably received in the opening, the guide device is positioned entirely external to the patient; a first suture configured to, when the shaft is releasably received in the opening, extend through a first one of the first plurality of holes, into the inner lumen of the shaft, and through the opening; and a second suture configured to, when the shaft is releasably received in the opening, extend through a second one of the first plurality of holes, into the inner lumen of the shaft, and through the opening.

11. The device of claim 10, wherein the one or more holes include a second plurality of holes, and when the shaft is releasably received in the opening, each one of the first plurality of holes is coaxially aligned with one of the second plurality of holes.

12. The device of claim 10, wherein the one or more holes include a single hole.

13. The device of claim 10, wherein the longitudinal axes of the first plurality of holes are substantially parallel to one another.

14. The device of claim 10, further comprising a suture capture device configured to be
- slidably moved in the opening in a first direction and then capture at least one suture extending through at least one of the first plurality of holes, and
- slidably moved in the opening in a second direction so as to slidably retract the captured at least one suture through the opening, the second direction being opposite to the first direction.

15. The device of claim 10, wherein the guide device includes a feature configured to position the shaft releasably received in the opening in a predetermined orientation relative to the guide device, the longitudinal axes of each of the first plurality of holes passing through the one or more holes when the shaft is in the predetermined orientation relative to the guide device.

16. The device of claim 15, wherein the feature includes at least one of a cut-out formed in the guide device, a visual mark on the guide device, and a tactile mark on the guide device.

17. A surgical device, comprising:
- a frame having a base portion and an arm portion extending transversely from the base portion, the base portion having an opening formed therethrough, and the arm portion having a plurality of holes formed therethrough, the opening formed through the base portion being configured to receive a surgical instrument therethrough, each of the plurality of holes being configured to receive a suture therethrough, a longitudinal axis of the opening formed through the base portion being substantially perpendicular to longitudinal axes of each of the plurality of holes, and the longitudinal axes of the plurality of holes being substantially parallel to one another;
- a first suture configured to, when a shaft is slidably seated in the opening, extend through a first one of the plurality of holes, into an inner lumen of the shaft, and through the opening formed through the base portion of the frame; and a second suture configured to, when the shaft is slidably seated in the opening, extend through a second one of the plurality of holes, into the inner lumen of the shaft, and through the opening formed through the base portion of the frame.

* * * * *